United States Patent
Bryan

(10) Patent No.: US 8,241,885 B2
(45) Date of Patent: Aug. 14, 2012

(54) ENGINEERED PROTEASES FOR AFFINITY PURIFICATION AND PROCESSING OF FUSION PROTEINS

(75) Inventor: Philip N. Bryan, North Potomac, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 12/887,692

(22) Filed: Sep. 22, 2010

(65) Prior Publication Data

US 2011/0008869 A1    Jan. 13, 2011

Related U.S. Application Data

(62) Division of application No. 10/567,073, filed as application No. PCT/US2004/021049 on Jun. 29, 2004, now Pat. No. 7,824,885.

(60) Provisional application No. 60/493,032, filed on Aug. 6, 2003.

(51) Int. Cl.
*C12N 9/54* (2006.01)
*C12P 21/06* (2006.01)
*C12N 9/56* (2006.01)
*C12N 15/57* (2006.01)
*C12N 15/75* (2006.01)

(52) U.S. Cl. .... 435/221; 435/68.1; 435/222; 435/252.3; 435/320.1; 536/23.2

(58) Field of Classification Search .................. None
See application file for complete search history.

(56) References Cited

U.S. PATENT DOCUMENTS

| | | | |
|---|---|---|---|
| 4,980,288 A | 12/1990 | Bryan et al. | |
| 4,990,452 A | 2/1991 | Bryan et al. | |
| 5,013,657 A | 5/1991 | Bryan et al. | |
| 5,116,741 A | 5/1992 | Bryan et al. | |
| 5,246,849 A | 9/1993 | Bryan et al. | |
| 5,260,207 A | 11/1993 | Pantoliano et al. | |
| 5,371,008 A | 12/1994 | Carter et al. | |
| 5,371,190 A | 12/1994 | Carter et al. | |
| 5,470,733 A | 11/1995 | Bryan et al. | |
| 5,567,601 A * | 10/1996 | Bryan et al. | .......... 435/222 |

(Continued)

FOREIGN PATENT DOCUMENTS

CA    2286861 A1    11/1998
(Continued)

OTHER PUBLICATIONS

Tsuchiya K., et al., 1994, "High level secretion of calf chymosin using a glucoamylase-prochymosin fusion gene in *Aspergillus oryzae*", Bioscience, Biotechnology, and Biochemistry, vol. 58, No. 5, pp. 895-899.*

(Continued)

*Primary Examiner* — Manjunath Rao
*Assistant Examiner* — William W Moore
(74) *Attorney, Agent, or Firm* — Hultquist PLLC; Kelly K. Reynolds; Steven J. Hultquist

(57) ABSTRACT

The present invention is directed to the identification of a protease prodomain that is capable of binding a corresponding protease with high affinity. The protease prodomain of the present invention is fused to a second protein to form a protease prodomain fusion protein. The presence of a protease prodomain protein in a fusion protein allows for easy and selective purification of the second protein by incubation with the corresponding protease.

8 Claims, 14 Drawing Sheets

Pro-domain

Subtilisin

U.S. PATENT DOCUMENTS

| | | | |
|---|---|---|---|
| 5,652,136 A | | 7/1997 | Carter et al. |
| 5,700,676 A | * | 12/1997 | Bott et al. .................. 435/221 |
| 5,707,848 A | | 1/1998 | Bryan et al. |
| 6,541,234 B1 | | 4/2003 | Bryan |
| 6,541,235 B1 | * | 4/2003 | Bryan .......................... 435/221 |
| 6,929,939 B2 | * | 8/2005 | Estell et al. .................. 435/220 |
| 7,098,002 B1 | | 8/2006 | Rubinstein et al. |
| 7,332,320 B2 | * | 2/2008 | Estell et al. .................. 435/219 |
| 7,531,325 B2 | | 5/2009 | Van Rooijen et al. |
| 7,824,885 B2 | * | 11/2010 | Bryan .......................... 435/69.7 |
| 2003/0166162 A1 | | 9/2003 | Van Rooijen et al. |
| 2006/0134740 A1 | | 6/2006 | Bryan et al. |

FOREIGN PATENT DOCUMENTS

WO     WO 2004/031733 A2 * 4/2004

OTHER PUBLICATIONS

Zhou, A., et al., 1995, "Structural elements that direct specific processing of different mammalian subtilisin-like prohormone convertases", `Journal of Biological Chemistry, vol. 270, No. 37, pp. 21509-21516.*

Walsh M. K., et al., 1996, "Investigating the use of the chymosin-sensitive sequence of kappa-casein as a cleavable linker site in fusion proteins", Journal of Biotechnology, vol. 45, No. 3, pp. 235-241.*

Fugere M. et al., 2002, "Inhibitory potency and specificity of subtilase-like pro-protein convertase (SPC) prodomains", The Journal of Biological Chemistry, vol. 277, No. 10, pp. 7648-7456.*

Fu, X. et al. , "Folding pathway mediated by an intramolecular chaperone", "Journal of Biological Chemistry", 2000, pp. 16871-16878, vol. 275, No. 22.

Kojima, S. et al."Accelerated refolding of substilisin BPN' by tertiary-structure-forming mutants of its propeptide", Journal of Biochemistry, 2001, vol. 130, No. 4, pp. 471-474.

Marie-Claire, C., et al., "Folding Pathway Mediated by an Intramolecular Chaperone: The Structural and Functional Characterization of the Aqualysin I Propeptide", Journal of Molecular Biology, vol. 305, No. 1, pp. 151-165, 2001.

Chowdhury, S.F., et al., "Design of noncovalent inhibitors of human cathepsin L. from the 96 residue proregion to optimized tripeptides", Journal of Medicinal Chemistry, vol. 45, No. 24, pp. 5321-5329, 2002.

Yabuta, Y. et al., "Folding Pathway Mediated by an Intramolecular Chaperone", Journal of Biological Chemistry, vol. 278, No. 17, pp. 15246-15251, 2003.

Abdulaev, N.G. et al., "Bacterial expression and one-step purification of an isotope-labelled heterotrimeric G-protein subunit", Journal of Biomolecular NMR, vol. 32, No. 1, pp. 31-40, 2005.

Strausberg, Susan et al., "Directed Coevolution of stability and catalytic activity in calcium-free substilisins" "Biochemistry", 2005, vol. 44, No. 9, pp. 3272-3279.

Almog, O. et al., "Structural Basis of Thermostability", "The Journal of Biological Chemistry", May 13, 2002, pp. 27553-27558, vol. 277, No. 30.

Baier, K. et al., "Evidence for propeptide assisted folding of calcium dependent protease of the *Cyanobacterium anabaena*", "European Journal of Biochemistry", Aug. 1996, pp. 750-755, vol. 241.

Bech, L. M. et al. , "Mutational replacements in substilisin 309", "European Journal of Biochemistry", May 1, 1992, pp. 869-874, vol. 209.

Bech, L. M. et al. , "Significance of Hydrophobic S4-P4 Interactions in Subtilisin 309 from *Bacillus*", "Biochemistry", Jan. 1993, pp. 2845-2852, vol. 32, No. 11.

Bryan, P. et al., "Energetics of Folding Subtilisin BPN'", "Biochemistry", Apr. 1, 1992, pp. 4937-4945, vol. 31, Publisher: American Chemical Society.

Bryan, P. et al., "Catalyis of a Protein Folding Reaction: Mechanistic Implications of the 2.0 A", "Biochemistry", Jun. 1995, pp. 10310-10318, vol. 34, Publisher: American Chemical Society.

Bryan, P. , "Protein Engineering of substilisin", "Biochimica et Biophysica Acta", Sep. 2000, pp. 203-222, vol. 1543.

Gron, Hanne, et al., "Studies of binding sites in the subtilisin from *Bacillus lentus* by means of site directed mutagenesis and kinetic investigations", "Subtilisin Enzymes: Practical Protein Engineering", 1996, pp. 105-112, Publisher: Plenum Press, Published in: New York.

Gron, Hanne, et al., "Interdependency of the binding subsites in substilisin", "Biochemistry", 1992, pp. 8967-8971, vol. 31, Publisher: American Chemical Society.

Hedstrom, L., "Serine Protease Mechanism and Specificity", Chem. Rev., Nov. 23, 2002, pp. 4501-4523, vol. 102.

Khan, A. et al., "Molecular mechanisms for the conversion of zymogens to active proteolytic enzymes", "Protein Science", 1998, pp. 815-836, vol. 7.

Marie-Claire, C. et al., "The Prosequence of Thermolysin Acts as an Intramolecular Chaperone when Expressed in trans with the Mature Sequence in E", "J. Mol. Biol.", 1999, pp. 1911-1915, vol. 285.

Nirasawa, Satoru et al., "Intramolecular chaperone and inhibitor activities of a propeplide from a bacterial zinc aminopeptidase", "Biochem. J.", 1999, pp. 25-31, vol. 341, Published in: GB.

Pantoliano, M. et al. , "Large Increases in General Stability for Subtilisin BPN through Incremental", "Biochemistry", Jun. 21, 1989, pp. 7205-7213, vol. 28, Publisher: American Chemical Society.

Perrona, J. et al., "Structural basis of substrate specificity in the serine proteases", "Protein Science", Jan. 1995, pp. 337-360, vol. 4.

Rheinnecker, M. et al., "Engineering a Novel Specificity in Subtilisin BPN'", "Biochemistry", Feb. 9, 1993, pp. 1199-1203, vol. 32, No. 5, Publisher: American Chemical Society.

Rheinnecker, M. et al., "Variants of Subtilisin BPN with Altered Specificity Profile", "Biochemistry", Feb. 9, 1993, pp. 221-225, vol. 33, Publisher: American Chemical Society.

Ruan, B. et al., "Stabilizing the Subtilisin BPN' pro-domain by phage display selection: how restrictive is the amino acid code for maximu", "Protein Science", Jul. 1998, pp. 2345-2353, vol. 7.

Ruan, B. et al., "Rapid Folding of Calcium-Free Subtilisin by a Stabilized Pro-Domain Mutant", "Biochemistry", May 4, 1999, pp. 8562-8571, vol. 38, No. 26, Publisher: American Chemical Society.

Ruan, B. et al., "Engineering Subtilisin into a Fluoride-Triggered Processing Protease Useful for One-Step Protein Purification", "Biochemistry", Oct. 31, 2004, pp. 14539-4546, vol. 43, No. 46, Publisher: American Chemical Society.

Ruan, B. et al., "Engineering Substrate Preference in Subtilisin: Structural and Kinetic Analysis of a Specificity Mutant", "Biochemistry", Apr. 30, 2008, pp. 6628-6636, vol. 47, No. 25, Publisher: American Chemical Society.

Ruvinov, S. et al., "Engineering the Independent Folding of he Substilisin BPN' Prodomain: Analysis of the Two-State Folding versus Protein", "Biochemistry", 1997, p. 10414-10421, vol. 36, Publisher: American Chemical Society.

Sauter, N. et al., "Structure of a-lytic protease complexed with its pro region", "nature structural biology", Nov. 1998, pp. 945-950, vol. 5, No. 11.

Shinde, U. et al., "Folding Pathway mediated by intramolecu ar chaperone", "Proc.Natl. Acad. Sci.", Aug. 1993, pp. 6924-6928, vol. 90.

Sorenson S. et al., "Mutational Replacements of the Amina Acid Residues Forming the Hydrophobic", , "Biochemistry", Jun. 1, 1993, pp. 8994-8999, vol. 32, Publisher American Chemical Society.

Strausberg, Susan et al., "Catalysis of a Protein Folding Reaction: Thermodynamic and Kinetic Analysis of Subtilisin BPN' Interactions with its Propeptide Fragment", "Biochemistry", May 19, 1993, pp. 8112-8119, vol. 32, No. 32, Publisher. American Chemical Society.

Vasantha, N. et al. , "Fusion of pro region of substilisin to staphylococcal protein A and its secretion by *Bacillus subtilis*", "Gene", 1986, pp. 23-28, vol. 49.

Ventura, S. et al., "Mapping the Pro-region of Carboxypeptidase B by Protein Engineering", "The Journal of Biological Chemistry", Jul. 9, 1999, pp. 19925-19933, vol. 274, No. 28.

Wang, L. et al., "Prodomain mutations at the Subtilisin Interface: Correlation of the binding energy and the rate of ctalyzed folding", "Biochemistry", Jan. 1995, pp. 415-420, vol. 15, Publisher: American Chemical Society.

Wang, L. et al., "Engineering the Independent Folding of the Subtilisin BPN' Pro-Domain: Correlation of Pro-Domain Stability with the Rate", "Biochemistry", Jan. 1998, pp. 3165-3171, vol. 37, No. 9, Publisher: American Chemical Society.

Wells, J et al., "Cloning, sequencing and secretion of *Bacillus amyloliqifacens* Subtilisin in *Bacillus subtilis*", "Nucleic Acids Research", Oct. 1983, pp. 7911-7925, vol. 11, No. 22.

Wetmore, D.R. et al., "Roles of the Propeptide and Metal Ions in the Folding and Stability of the Catalytic Domain of Stromelysin (Matrix Metal", "Biochemistry", 1996, pp. 6549-6558, vol. 35.

Winther, J. et al., "Propeptide of carboxypeptidase Y provides a chaperone-like function as well as inhibition of the enzymatic activity", "Proc. Natl. Acad. Sci.", Oct. 1991, pp. 9330-9334, vol. 88.

Yamamoto, Yoshimi et al., "Proregion of *Bombyx mori* Cysteine Proteinase Functions as an Intramolecular Chaperone to Promote Proper Folding of the M", "Archives of Insect Biochemistry and Physiology", Jun. 1999, pp. 167-178, vol. 42.

Ohta, Y. et al., "Pro-peptide as an intermolecular chaperone: renaturation of denatured subtilisin E with a synthetic pro-peptide", Molecular Microbiology, 1991, vol. 5, No. 6, pp. 1507-1510.

Egnell, P. et al.,"The subtilisin Carlsberg pro-region is a memorane anchorage for two fusion proteins produced in *Bacillus subtilis*", Gene, vol. 97, No. 1, pp. 49-54, 1991.

Jordan, F. et al.,"Proton NMR of the active center of serine proteases complexed to slow- and rapid-binding inhibitors and to pro-peptide of subtilisin E, a protein-protease inhibitor", Journal of Cellular Biochemistry Supplement, 1993, vol. 0, No. 17, Part C. p. 295, Abstract No. LZ 425.

Hu, Z. et al., "Further evidence for the structure of the subtilisin propeptide and for its interactions with a mature subtilisin", Journal of Biological Chemistry, 1996, vol. 271, No. , pp. 3375-3384.

Volkov, A. et al., "Evidence for intromolecular processing of prosubtilisin sequestered on a solid support", Journal of Molecular Biology, vol. 262, pp. 595-599, 1996.

* cited by examiner

```
Ala Gln Ser Val Pro Tyr Gly Val Ser Gln Ile Lys Ala Pro Ala Leu
 1               5                  10                  15
His Ser Gln Gly Tyr Thr Gly Ser Asn Val Lys Val Ala Val Ile Asp
                20                  25                  30
Ser Gly Ile Asp Ser Ser His Pro Asp Leu Lys Val Ala Gly Gly Ala
                35                  40                  45
Ser Met Val Pro Ser Glu Thr Asn Pro Phe Gln Asp Asn Asn Ser His
     50                  55                  60
Gly Thr His Val Ala Gly Thr Val Ala Ala Leu Asn Asn Ser Ile Gly
 65                  70                  75                  80
Val Leu Gly Val Ala Pro Ser Ala Ser Leu Tyr Ala Val Lys Val Leu
                 85                  90                  95
Gly Ala Asp Gly Ser Gly Gln Tyr Ser Trp Ile Ile Asn Gly Ile Glu
                100                 105                 110
Trp Ala Ile Ala Asn Asn Met Asp Val Ile Asn Met Ser Leu Gly Gly
             115                 120                 125
Pro Ser Gly Ser Ala Ala Leu Lys Ala Ala Val Asp Lys Ala Val Ala
         130                 135                 140
Ser Gly Val Val Val Ala Ala Ala Gly Asn Glu Gly Thr Ser Gly
145                 150                 155                 160
Ser Ser Ser Thr Val Gly Tyr Pro Gly Lys Tyr Pro Ser Val Ile Ala
                165                 170                 175
Val Gly Ala Val Asp Ser Ser Asn Gln Arg Ala Ser Phe Ser Ser Val
             180                 185                 190
Gly Pro Glu Leu Asp Val Met Ala Pro Gly Val Ser Ile Gln Ser Thr
         195                 200                 205
Leu Pro Gly Asn Lys Tyr Gly Ala Tyr Asn Gly Thr Ser Met Ala Ser
     210                 215                 220
Pro His Val Ala Gly Ala Ala Ala Leu Ile Leu Ser Lys His Pro Asn
225                 230                 235                 240
Trp Thr Asn Thr Gln Val Arg Ser Ser Leu Glu Asn Thr Thr Thr Lys
                245                 250                 255
Leu Gly Asp Ser Phe Tyr Tyr Gly Lys Gly Leu Ile Asn Val Gln Ala
             260                 265                 270
Ala Ala Gln
        275
```

Figure 2

TABLE 1

| | S149 | S160 | S188 | S189 | S190 | S191 | S193 | S194 | S196 | S197 | S198 | S199 | S201 | S202 |
|---|---|---|---|---|---|---|---|---|---|---|---|---|---|---|
| Q2K | X | X | X | X | X | X | X | X | X | X | X | X | X | X |
| S3C | X | X | X | X | X | X | X | X | X | X | X | X | X | X |
| P5S | X | X | X | X | X | X | X | X | X | X | X | X | X | X |
| S9A | X | X | X | X | X | X | X | X | X | X | X | X | X | X |
| I31L | X | X | X | X | X | X | X | X | X | X | X | X | X | X |
| K43N | X | X | X | X | X | X | X | X | X | X | X | X | X | X |
| M50F | X | X | X | X | X | X | X | X | X | X | X | X | X | X |
| A73L | X | X | X | X | X | X | X | X | X | X | X | X | X | X |
| Δ75-83 | X | X | X | X | X | X | X | X | X | X | X | X | X | X |
| E156S | X | X | X | X | X | X | X | X | X | X | X | X | X | X |
| G166S | X | X | X | X | X | X | X | X | X | X | X | X | X | X |
| G169A | X | X | X | X | X | X | X | X | X | X | X | X | X | X |
| S188P | X | X | X | X | X | X | X | X | X | X | X | X | X | X |
| Q206C | X | X | X | X | X | X | X | X | X | X | X | X | X | X |
| N212G | X | X | X | X | X | X | X | X | X | X | X | X | X | X |
| K217L | X | X | X | X | X | X | X | X | X | X | X | X | X | X |
| N218S | X | X | X | X | X | X | X | X | X | X | X | X | X | X |
| T254A | X | X | X | X | X | X | X | X | X | X | X | X | X | X |
| Q271E | X | X | X | X | X | X | X | X | X | X | X | X | X | X |
| Y104A | | X | X | X | X | X | X | X | X | X | X | X | X | X |
| G128S | | X | X | X | X | X | X | X | X | X | X | X | X | X |
| L126I | | | | | | | | | | | | | | |
| S166G | | | | | | X | | | | | | X | X | X |
| N155L | | | X | | | | | | | | | | | |
| D32A | | | | X | | | | | | | | | X | |
| D32S | | | | | X | | | | | | | | | |
| D32V | | | | | | | | | X | | | X | | |
| D32T | | | | | | | | | | X | | | | |
| D32G | | | | | | | | | | | X | | | |
| N155Q | | | | | | X | | | | | | | | |
| S221A | | | | | | | | X | | | | | | X |

Figure 3

CDC6

DNA replication factor
379 aa

Methanothermobacter
thermautotrophicus

SEQUENCE LISTING

```
<160> NUMBER OF SEQ ID NOS: 14

<210> SEQ ID NO 1
<211> LENGTH: 30
<212> TYPE: PRT
<213> ORGANISM: Bacillus amyloliquefaciens

<400> SEQUENCE: 1

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala
            20                  25                  30

<210> SEQ ID NO 2
<211> LENGTH: 77
<212> TYPE: PRT
<213> ORGANISM: Bacillus amyloliquefaciens

<400> SEQUENCE: 2

Ala Gly Lys Ser Asn Gly Glu Lys Lys Tyr Ile Val Gly Phe Lys Gln
1               5                   10                  15

Thr Met Ser Thr Met Ser Ala Ala Lys Lys Lys Asp Val Ile Ser Glu
            20                  25                  30

Lys Gly Gly Lys Val Gln Lys Gln Phe Lys Tyr Val Asp Ala Ala Ser
        35                  40                  45

Ala Thr Leu Asn Glu Lys Ala Val Lys Glu Leu Lys Lys Asp Pro Ser
    50                  55                  60

Val Ala Tyr Val Glu Glu Asp His Val Ala His Ala Tyr
65                  70                  75

<210> SEQ ID NO 3
<211> LENGTH: 275
<212> TYPE: PRT
<213> ORGANISM: Bacillus amyloliquefaciens

<400> SEQUENCE: 3

Ala Gln Ser Val Pro Tyr Gly Val Ser Gln Ile Lys Ala Pro Ala Leu
1               5                   10                  15
```

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
            35                  40                  45

Ser Met Val Pro Ser Glu Thr Asn Pro Phe Gln Asp Asn Asn Ser His
 50                      55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                    85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
                115                 120                 125

Pro Ser Gly Ser Ala Ala Leu Lys Ala Ala Val Asp Lys Ala Val Ala
                130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
                195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
                260                 265                 270

Ala Ala Gln
275

<210> SEQ ID NO 4
<211> LENGTH: 75
<212> TYPE: PRT
<213> ORGANISM: Artificial Sequence
<220> FEATURE:
<223> OTHER INFORMATION: pR8 variant of SEQ ID NO: 2

<400> SEQUENCE: 4

Ala Gly Lys Ser Asn Gly Glu Lys Lys Tyr Ile Val Gly Phe Lys Ser
 1               5                  10                  15

Gly Ile Lys Ser Cys Ala Lys Lys Gln Asp Val Ile Ser Glu Lys Gly
            20                  25                  30

Gly Lys Leu Gln Lys Cys Phe Lys Tyr Val Asp Ala Ala Ser Ala Thr
            35                  40                  45

Leu Asn Glu Lys Ala Val Lys Glu Leu Lys Lys Asp Pro Ser Val Ala
 50                  55                  60

Tyr Val Glu Glu Asp Lys Val Ala Lys Ala Tyr
 65                  70                  75

<210> SEQ ID NO 5
<211> LENGTH: 75
<212> TYPE: PRT

```
<213> ORGANISM: Artificial Sequence
<220> FEATURE:
<223> OTHER INFORMATION: pR8FKAM variant of SEQ ID NO: 2

<400> SEQUENCE: 5

Ala Gly Lys Ser Asn Gly Glu Lys Lys Tyr Ile Val Gly Phe Lys Ser
1               5                   10                  15

Gly Ile Lys Ser Cys Ala Lys Lys Gln Asp Val Ile Ser Glu Lys Gly
            20                  25                  30

Gly Lys Leu Gln Lys Cys Phe Lys Tyr Val Asp Ala Ala Ser Ala Thr
        35                  40                  45

Leu Asn Glu Lys Ala Val Lys Glu Leu Lys Lys Asp Pro Ser Val Ala
    50                  55                  60

Tyr Val Glu Glu Asp Lys Val Phe Lys Ala Met
65                  70                  75

<210> SEQ ID NO 6
<211> LENGTH: 75
<212> TYPE: PRT
<213> ORGANISM: Artificial Sequence
<220> FEATURE:
<223> OTHER INFORMATION: pR58 (pR8FRAM) variant of SEQ ID NO: 2

<400> SEQUENCE: 6

Ala Gly Lys Ser Asn Gly Glu Lys Lys Tyr Ile Val Gly Phe Lys Ser
1               5                   10                  15

Gly Ile Lys Ser Cys Ala Lys Lys Gln Asp Val Ile Ser Glu Lys Gly
            20                  25                  30

Gly Lys Leu Gln Lys Cys Phe Lys Tyr Val Asp Ala Ala Ser Ala Thr
        35                  40                  45

Leu Asn Glu Lys Ala Val Lys Glu Leu Lys Lys Asp Pro Ser Val Ala
    50                  55                  60

Tyr Val Glu Glu Asp Lys Val Phe Arg Ala Met
65                  70                  75

<210> SEQ ID NO 7
<211> LENGTH: 9
<212> TYPE: PRT
<213> ORGANISM: Artificial Sequence
<220> FEATURE:
<223> OTHER INFORMATION: C-terminal portion of prodomain
<220> FEATURE:
<221> NAME/KEY: VARIANT
<222> LOCATION: (6)..(6)
<223> OTHER INFORMATION: Xaa is Phe or Tyr
<220> FEATURE:
<221> NAME/KEY: VARIANT
<222> LOCATION: (9)..(9)
<223> OTHER INFORMATION: Xaa is Met, Lys or Tyr

<400> SEQUENCE: 7

Glu Glu Asp Lys Leu Xaa Gln Ser Xaa
1               5

<210> SEQ ID NO 8
<211> LENGTH: 6
<212> TYPE: PRT
<213> ORGANISM: Artificial Sequence
<220> FEATURE:
<223> OTHER INFORMATION: Residues 16-21 of SEQ ID NO: 2

<400> SEQUENCE: 8

Gln Thr Met Ser Thr Met
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Substitution of residues 16-21 of subtilisin
      prodomain

<400> SEQUENCE: 9

Ser Gly Ile Lys
1

<210> SEQ ID NO 10
<211> LENGTH: 4
<212> TYPE: PRT
<213> ORGANISM: Artificial Sequence
<220> FEATURE:
<223> OTHER INFORMATION: Substitution of P1-P4 of subtilisin prodomain

<400> SEQUENCE: 10

Phe Lys Ala Met
1

<210> SEQ ID NO 11
<211> LENGTH: 4
<212> TYPE: PRT
<213> ORGANISM: Artificial Sequence
<220> FEATURE:
<223> OTHER INFORMATION: Substitution of P1-P4 of subtilisin prodomain

<400> SEQUENCE: 11

Phe Lys Ala Tyr
1

<210> SEQ ID NO 12
<211> LENGTH: 4
<212> TYPE: PRT
<213> ORGANISM: Artificial Sequence
<220> FEATURE:
<223> OTHER INFORMATION: Substitution of P1-P4 of subtilisin prodomain

<400> SEQUENCE: 12

Phe Lys Ala Phe
1

<210> SEQ ID NO 13
<211> LENGTH: 4
<212> TYPE: PRT
<213> ORGANISM: Artificial Sequence
<220> FEATURE:
<223> OTHER INFORMATION: P1-P4 of wild-type subtilisin prodomain

<400> SEQUENCE: 13

Ala His Ala Tyr
1

<210> SEQ ID NO 14
<211> LENGTH: 4
<212> TYPE: PRT
<213> ORGANISM: Artificial Sequence
<220> FEATURE:
<223> OTHER INFORMATION: Substitution of P1-P4 of subtilisin prodomain

<400> SEQUENCE: 14

Phe Arg Ala Met
1
```

ENGINEERED PROTEASES FOR AFFINITY PURIFICATION AND PROCESSING OF FUSION PROTEINS

CROSS-REFERENCE TO RELATED APPLICATIONS

This application is a divisional of U.S. patent application Ser. No. 10/567,073, filed Mar. 7, 2006 and published as U.S. Patent Application Publication No. 2006/0134740 on Jun. 22, 2006 and issued as U.S. Pat. No. 7,824,885 on Nov. 2, 2010, which was filed under the provisions of 35 U.S.C. §371 and claims the priority of International Patent Application No. PCT/US2004/021049, filed Jun. 29, 2004 and published as International Publication No. WO 2005/017110 on Feb. 24, 2005, which claims the benefit of priority under 35 USC §119(e) of U.S. Provisional Patent Application No. 60/493,032 filed Aug. 6, 2003. The disclosures of said applications are hereby incorporated herein by reference, in their respective entireties, for all purposes.

BACKGROUND OF THE INVENTION

1. Field of the Invention

The present invention relates to purification methods, and more particularly, to a fusion protein comprising a target protein and a protease prodomain protein wherein the prodomain protein has high affinity for binding with a corresponding protease or variant thereof to provide a protease binding complex for subsequent recovery of the target protein.

2. Description of Related Art

Recombinant DNA techniques have facilitated the expression of proteins for diverse applications in medicine and biotechnology. However, the purification of recombinant proteins is often complicated and problematic. The large-scale, economic purification of proteins generally includes producing proteins by cell culture, such as bacterial cell lines engineered to produce the protein of interest by insertion of a recombinant plasmid containing the gene for that protein. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different techniques. As part of the overall recovery process for the protein, the protein may be exposed to an immobilized reagent, which binds to the protein.

Proteomics initiatives of the post genomic era have greatly increased the demand for rapid, effective and standardized procedures for the purification and analysis of proteins. For example, recombinant proteins are frequently fused with other proteins or peptides to facilitate purification. The fused domain serves as a temporary hook for affinity purification and ultimately must be cleaved off by site-specific proteolysis. A number of fusion protein systems using different carrier proteins are now commercially available, particularly for *E. coli* expression. Examples include maltose binding protein, glutathione S-transferase, biotin carboxyl carrier protein, thioredoxin and cellulose binding domain.

Fusion protein expression simplifies the separation of recombinant protein from cell extracts by affinity chromatography using an immobilized, moderate-affinity ligand specific to the carrier protein. However, typically, immobilization requires the covalent attachment of the ligand to the matrix resulting, in many cases, in loss of activity. A typical example of a widely used product is Protein A-Sepharose. This highly expensive product is used for the purification of IgG by affinity chromatography, as well as for many diagnostic protocols.

Thus, more economical and technically simple methods for purification of soluble proteins, which do not involve scale-up of chromatographic procedures, are therefore desirable.

The function of proteases range from broad specificity, degradative enzymes to highly sequence specific enzymes that regulate physiological processes from embryonic development to cell death. Some high specificity proteases have been recruited from nature to serve as tools for the purification and analysis of proteins in a manner somewhat analogous to use of restriction endonucleases to manipulate DNA. The specific processing enzymes currently available are from mammalian sources, such as thrombin, factor Xa and Enteropeptidase. However, although widely used in protein work these natural enzymes are very expensive and of low stability limiting their usefulness for many applications.

Considerable effort has been devoted to engineering robust, bacterial proteases, such as subtilisin, to cleave defined sequences. Subtilisin is a serine protease produced by Gram-positive bacteria or by fungi. Subtilisins are important industrial enzymes as well as models for understanding the enormous rate enhancements affected by enzymes. The amino acid sequences of numerous subtilisins are known and include subtilisins from *Bacillus* strains, for example, subtilisin BPN', subtilisin Carlsberg, subtilisin DY, subtilisin amylosacchariticus, and mesenticopeptidase. For these reasons along with the timely cloning of the gene, ease of expression and purification and availability of atomic resolution structures, subtilisin became a model system for protein engineering studies in the 1980's. Fifteen years later, mutations in well over 50% of the 275 amino acids of subtilisin have been reported in the scientific literature. Most subtilisin engineering has involved catalytic amino acids, substrate binding regions and stabilizing mutations. The most mutagenized subtilisins (Neet K E, et al., *Proc Natl Acad Sci USA* 1966, 56:1606-1611; Polgar L, et al., *Biochemistry* 1967, 6:610-620) are those secreted from the *Bacillus* species *amyloliquefaciens* (BPN'), *subtilis* (subtilisin E) and *lentus* (Savinase).

In spite of the intense activity in protein engineering of subtilisin it previously has not been possible to transform it from a protease with broad substrate preferences into an enzyme suitable for processing specific substrates thereby rendering it useful for protein recovery systems. Thus, it would be extremely useful for research and protein purifica-

SUMMARY OF THE INVENTION

The invention relates to the discovery that subtilisin and variants thereof are useful in the purification of proteins when used with a substrate sequence of high affinity for the protease, wherein the substrate sequence is preferably the prodomain of subtilisin. Also, disclosed is the construction of an expression system for the production of a fusion protein comprising the prodomain of subtilisin and a second protein of interest.

Secreted proteases, such as subtilisin, are synthesized as inactive zymogen precursors in order to tightly regulate the timing of protease activation (Khan A R, et al., *Protein Sci* 1998, 7:815-836). Frequently, the zymogen precursor consists of N-terminal amino acids attached to the mature protease sequence. A number of these N-terminal extensions (prodomains) are large enough to fold independently and have been shown to bind tightly to the active site of the mature protease (Shinde U, et al., *Adv Exp Med Biol* 1996, 379:147-154; Agard D A, et al., *Science* 1993, 260:1903-1904; Baker D, et al., *Curr Opin Cell Biol* 1993, 5:966-970; Baker D, et al., *Biochemistry* 1994, 33:7505-7509; Baker D: et al., *Nat Struct Biol* 1998, 5:1021-1024; Inouye M, *Enzyme* 1991, 45:314-321; Shinde U, et al., *Proc. Natl. Acad. Sci. USA* 1993, 90:6924-6928; Shinde U, et al., *TIBS* 1993, 18:442-446).

Subtilisin BPN is an extracellular serine proteinase from *Bacillus amyloliquefaciens* having a primary translation product which is a pre-pro-protein (Wells J A, et al., *Nucleic Acids Res.* 1983, 11:7911-7925; Vasantha N, et al., *J. Bacteriol.* 1984, 159:811-819). A 30 amino acid pre-sequence (SEQ ID NO. 1) serves as a signal peptide for protein secretion across the membrane and is hydrolyzed by a signal peptidase (Bryan P N, *Chem Rev* 2002, 102:4805-4816). The extracellular part of the maturation process involves folding of prosubtilisin, self-processing of a 77 amino acid sequence (SEQ ID NO. 2), to produce a processed complex and finally degradation of the prodomain to create the 275 amino acid (SEQ ID NO. 3) mature SBT sequence. The 77 amino acid prodomain is removed autocatalytically and it has been suggested that the prodomain delays the activation of a subtilisin until after secretion from *Bacillus* (Wong S, et al., *J. Biol. Chem.* 1986, 261:10176-10181) because the prodomain is a competitive inhibitor of the active subtilisin ($K_i$ of $5.4 \times 10^{-7}$ M) exhibiting a strong inhibition of the activity of the subtilisin.

Subtilisin's broad preferences result from the manner in which it binds to protein substrates. Most subtilisin contacts are with the first four amino acids on the acyl side of the scissile bond located in the substrate structure. These residues are denoted P1 through P4, numbering from the scissile bond toward the N-terminus of the substrate (Berger A, et al., *Philos Trans R Soc Lond B Biol Sci* 1970, 257:249-264). The side chain components of substrate binding result primarily from the P1 and P4 amino acids (Estell D A, et al., *Science* 1986, 233:659-663; Gron H, et al., *Biochemistry* 1992, 31:8967-8971; Gron H, et al., *Biochemistry* 1992, 31:6011-6018). Subtilisin prefers hydrophobic amino acids at these positions. A high resolution structure of a complex between subtilisin and prodomain shows that the C-terminal portion of the prodomain binds as a substrate into the subtilisin active site and that the globular part of the prodomain has an extensive complementary surface to subtilisin. The C-terminal residues extend out from the central part of the prodomain and bind in a substrate-like manner along SBT's active site cleft. Thus, residues Y77, A76, H75 and A74 of the prodomain act as P1 to P4 substrate amino acids, respectively. These residues conform to subtilisin's natural sequence preferences. The folded prodomain has shape complementary and high affinity to native subtilisin mediated by both the substrate interactions of the C-terminal tail and a hydrophobic interface provided by the β-sheet (Gallagher T D, et al., *Structure* 1995, 3:907-914).

Likewise, sequencing of the gene for alkaline phosphatase (ALP) revealed that ALP is also synthesized as a pro-enzyme. In ALP, the prodomain (166 amino acids) is almost as large as the mature protease (198 amino acids). Further, it was demonstrated that the ALP prodomain is required to produce active ALP in vivo and that the 166 amino acid prodomain was a strong competitive inhibitor of ALP (Silen J L, et al., *Gene* 1988, 69:237-244). Interestingly, structure analysis of the ALP with its prodomain revealed an affinity binding of the prodomain to the active site of ALP (Yamamoto Y, et al., *Arch Insect Biochem Physiol* 1999, 42:167-178).

Other examples of prodomain mediated folding have been found in all four mechanistic families of proteases: serine proteases (Winther J R, et al., *Proc Natl Acad Sci USA* 1991, 88:9330-9334; Zhou Y, et al., *J Biol Chem* 1993, 268:5615-5623; Baier K, et al., *Eur Biochem* 1996, 241:750-755; Fabre E, et al., *J Biol Chem* 1991, 266:3782-3790; Fabre E, et al., *J Biol Chem* 1992, 267:15049-15055; Chang Y C, et al., *Biochem Biophys Res Commun* 1996, 219:463-468); Aspartic proteases (Baardsnes J, et al., *J Bacteriol* 1998, 180:3241-3244; van den Hazel H B, et al., *J Biol Chem* 1993, 268:18002-18007; Cawley N X, et al., *J Biol Chem* 1998, 273:584-591); metalloproteases (Fukuda R, et al., *J Biol Chem* 1994, 269:9556-9561; Nirasawa S, et al., *Biochem J* 1999, 341 (Pt 1):25-31; Marie-Claire C, et al., *J Mol Biol* 1999, 285:1911-1915; Cao J, et al., *J Biol Chem* 2000, 275:29648-29653; Ventura S, et al., *J Biol Chem* 1999, 274:19925-19933); and cysteine proteases (Wetmore D R, et al., *Biochemistry* 1996, 35:6549-6558).

Thus, in one aspect the present invention relates to protein purification processes using a prodomain protein linked to a target protein wherein the prodomain protein has a high affinity for the normally associated protease thereby providing for easy separation of the target protein from the prodomain. Preferably, the present invention relates to the prodomain of secreted proteases such as subtilisin or variants thereof, wherein the prodomain has a high affinity for the subtilisin or variants thereof.

In another aspect, the present invention relates to a fusion protein comprising a protease prodomain fused to target protein, wherein cleavage is directed specifically to the peptide bond joining the prodomain and the target protein and wherein the prodomain has a high affinity binding for the corresponding protease. Preferably, the protease is subtilisin or a variant thereof, wherein the variant is modified to specifically hydrolyze the peptide bond between the protease prodomain and a target protein and/or whose hydrolytic activity may be triggered by specific ions. Additionally, the prodomain protein may be optimized by including cognate sequences for the protease.

In yet another aspect, the present invention comprises a prodomain protein of amino acid sequence SEQ ID NO. 2 fused to a protein of interest. Further the prodomain sequence may comprise substitutions in at least the P1-P4 amino acid residues including the following:

| Prodomain | P4 | P3 | P2 | P1 |
|---|---|---|---|---|
| Wild-type | A | H | A | Y |
| Substitutions | F or Y | any | A or S | M, Y, F, H or L |

Several cognate sequences have been found to be highly effective including FKAM (SEQ ID NO: 10), FKAY (SEQ ID NO: 11) or FKAF (SEQ ID NO: 12). Surprising the addition of the sequences FKAM (SEQ ID NO: 10), FKAY (SEQ ID NO: 11) or FKAF (SEQ ID NO: 12) also increase the affinity of the prodomain to the subtilisin to $>10^9$ M$^{-1}$.

Additionally, the subtilisin prodomain may further include stabilizing mutations to further increase its affinity for subtilisin. Still further, mutations may be incorporated into one or more of the four catalytic amino acids of subtilisin to drastically reduce its proteolysis of non-specific amino acid sequences. Preferred mutations are included at amino acid positions 32, 64, 155 and 221 of the subtilisin sequence identified as SEQ ID NO. 3 and shown in FIG. 2.

Thus, in another aspect, the present invention provides for a processing protease having a $K_m$ for a cognate sequence in the prodomain that is <1 nm. The $k_{cat}$ of a processing protease is in the range of $10^{-1}$ seq$^{-1}$ to $10^{-5}$ seq$^{-1}$. Thus the turnover number ($k_{cat}/K_m$) for the processing protease and its cognate prodomain substrate is in the range of $10^4$ M$^{-1}$ s$^{-1}$ to $10^8$ M$^{-1}$ s$^{-1}$ while turnover number vs. a non-specific sequence is <1 M$^{-1}$ s$^{-1}$.

A preferred processing enzyme would prefer its cognate prodomain by $>10^6$ fold over a non-specific sequence. The most preferred embodiments of the invention are processing subtilisins that have $k_{cat}$ values in the range of 0.001 to 0.0001 s$^{-1}$. Subtilisins that cleave in this time range process the substrate slowly enough to allow affinity purification of any protein containing the cognate prodomain as an N-terminal fusion domain.

In another aspect the present invention provides for a fusion protein comprising a target protein linked to a domain, wherein the domain protein includes amino acid residues on the C-terminal comprising a variant of (E E D K L (F/Y) Q S (M/L/Y) (SEQ ID NO: 7), wherein the C-terminal part of the domain causes an affinity for subtilisin or variants thereof.

In yet another aspect, the present invention provides for a method of generating a subtilisin prodomain fusion product. An exemplary procedure comprises the following steps:

providing a nucleic acid encoding the subtilisin prodomain fusion protein wherein the fusion protein comprises a prodomain of subtilisin or variant thereof and a second protein of interest, the prodomain being capable of binding subtilisin or variant thereof with high affinity;

transfecting a host cell with the nucleic acid or using an equivalent means for introducing the nucleic acid into the host cell; and culturing the transformed host cell under conditions suitable for expression of the fusion protein.

The subject fusion protein will generally be produced by recombinant methods, in particular and preferably by expression of a subtilisin prodomain/second protein DNA wherein the DNA will be expressed in microbial host cells, in particular *Bacillus subtilis*, because this bacteria naturally produces subtilisin, is an efficient secretor of proteins, and is able to produce the prodomain protein in an active conformation. However, the invention is not restricted to the expression of the fusion protein in *Bacillus*, but rather embraces expression in any host cell that provides for expression of the fusion protein. Suitable host cells for expression are well known in the art and include, e.g., bacterial host cells such as *Escherichia coli, Bacillus, Salmonella, Pseudomonas*; yeast cells such as *Saccharomyces cerevisiae, Pichia pastoris, Kluveromyces, Candida, Schizosaccharomyces*; and mammalian host cells such as CHO cells. Bacterial host cells, however, are the preferred host cells for expression.

Expression of the DNA encoding the subtilisin prodomain/second protein fusion protein may use available vectors and regulatory sequences. The actual selection will depend in a large part upon the particular host cells that are utilized for expression. For example, if the fusion protein is expressed in *Bacillus*, a *Bacillus* promoter will generally be utilized as well as a *Bacillus* derived vector. Expression of the fusion protein in microbial host cells will generally be preferred since this will allow for the microbial host cell to produce the subtilisin prodomain in a proper conformation.

A further aspect of the present invention relates to a method for purifying a protein of interest from a fusion protein and separation therefrom, the method comprising:

contacting a fusion protein comprising a prodomain protein linked to the protein of interest with an effective amount of a subtilisin or variant thereof under conditions suitable for the formation of a binding complex between the subtilisin or variant thereof and the prodomain protein of the fusion protein;

incubating the binding complex for a sufficient time for the subtilisin or variant thereof to cleave the protein of interest from the binding complex; and recovering the protein of interest Preferably, the protease has been modified to specifically bind to the protease prodomain fusion protein and the protease prodomain protein has been modified to included cognate sequences of the protease for autocatalytic removal of the second protein from the binding complex. More preferably, the protease is subtilisin or a variant thereof and the prodomain has a high binding affinity for such protease.

Yet another aspect of the present invention provides nucleic acid encoding a fusion protein comprising a protease prodomain protein and a second target protein including a cleavage site positioned therebetween. Preferably, the cleavage site is upstream of the N-terminal amino acid of the second protein of the fusion product. More preferably, the cleavage site is downstream from the P4-P1 amino acid residues.

Cleavage point
↓

Prodomain P4 P3 P2 P1 TARGET PROTEIN

Another aspect of the present invention provides for a host cell comprised of nucleic acid encoding a protease prodomain fusion protein of the present invention.

An additional aspect of the present invention relates to a diagnostic kit for the detection of a substance of interest comprising:

(a) a protease prodomain fusion protein comprising:
(i) a protease prodomain capable of binding to a subtilisin or variant thereof with high affinity; and
(ii) a second protein capable of binding a substance of interest;

(b) a detectable label; and (c) a subtilisin or variant thereof for binding to the protease prodomain fusion protein.

Preferably, the prodomain is a subtilisin prodomain and the second protein may include, but is not limited to an enzyme, hormone, antigen, or antibody.

In another aspect, the present invention relates to an assay method for using the above described diagnostic kit for detecting the presence of a substance of interest in a test sample comprising:
(a) incubating a test sample, which may contain a substance of interest, with a sufficient amount of a protease prodomain fusion protein, wherein the protease prodomain fusion protein comprises:
   (i) a protease prodomain capable of binding with high affinity to a subtilisin or variant thereof, and
   (ii) a second protein capable of binding the substance of interest,
wherein the incubating conditions permit the binding of the substance of interest to the second protein;
(b) contacting the protease prodomain fusion protein used in step (a) to subtilisin or a variant thereof, wherein the subtilisin or a variant thereof is in solution in an amount effective to bind the fusion protein and form a binding complex or immobilized on a solid phase to form a subtilisin/prodomain fusion protein binding complex;
(c) incubating the subtilisin/prodomain fusion protein binding complex for a sufficient time for autocatalytic cleavage of the second protein from the binding complex;
(d) recovering the second protein bound to the substance of interest.

This embodiment further provides for introducing a detectable label wherein the label is capable of binding to the substance of interest; and determining the presence or absence of the label, to provide an indication of the presence or absence of the substance of interest in the test sample. The detectable label may be introduced either before separation of the second protein from the binding complex or after the second protein is recovered.

The test sample may be a bodily fluid, including, but not limited to, blood, urine, semen, saliva, mucus, tears, vaginal secretions, and the like.

In a specific embodiment of the present invention, the method is designed for the detection of a specific protein or peptide in a testing sample, thus, the second protein of the prodomain subtilisin fusion protein may be an antibody against the specific protein or peptide in the testing sample. The antibody may be a monoclonal antibody or a polyclonal antibody. The subtilisin prodomain of the present invention may be conjugated to the antibody either directly or through a linker moiety.

The substance of interest may also comprise a biotinylated probe bound to a protein, peptide, hormone, nucleic acid or other probe-targetable molecule. The label may include an enzyme, that upon adding a sufficient amount of a substrate for the enzyme, the substrate is converted by the enzyme to a detectable compound.

Finally, it is a further aspect of the present invention to provide a drug delivery system comprising a subtilisin prodomain protein associated with a therapeutic compound or drug of interest to form a fusion product, wherein the fusion product is further complexed to a subtilisin or variant thereof to form a drug delivery complex. In such a drug delivery system, the drug of interest may be conjugated to the subtilisin prodomain either directly or through a linker moiety. Many methods of conjugation exist and are known in the art. For example, acyl activation agents exist, such as cyclohexylcarbodiimide, which can be used to form amide or ester bonds.

In one embodiment such a drug delivery system can be a slow or sustained drug delivery system wherein the drug of interest is slowly released from the subtilisin prodomain bound to subtilisin. It is contemplated that such a drug delivery system can be incorporated into a composition that can be administered parenterally, orally, topically or by inhalation. Furthermore, the composition may be in the form of a solid, gel, liquid or aerosol.

Other features and advantages of the invention will be apparent from the following detailed description, drawings and claims.

BRIEF DESCRIPTION OF THE FIGURES

FIG. 2 shows the amino acid sequence of Subtilisin BPN' wild type.

FIG. 3 shows Table 1 setting forth mutations introduced to subtilisin 'BPN.

Figure 1:
FIG. 1 illustrates a ribbon drawing depicting the $\alpha$-carbon backbone of subtilisin in complex with its prodomain.

Lane 1: Molecular weight standards—2 µg band
Lane 2: BL21 DE3 cell lysate—10 µl of 50 ml from 1 L culture of 671 (pR58FKAM-$G_B$)
Injected 1 ml of lysate on S189HT1 column:
Lane 3: flow through loaded at 1 ml/min (10 µl of 2 ml fraction 2)
Lane 4: flow through loaded at 1 ml/min (10 µl of 2 ml fraction 3)
Lane 5: cleavage/elution by 0.1M KF. (10 µl of 1 ml fraction 1; ~7 µg total)
Lane 6: cleavage/elution by 0.1M KF. (10 µl of 1 ml fraction 2; ~3 µg total)
Lane 7: strip by 0.1 M $H_3PO_4$ (10 µl of 1 ml fraction 1; ~10 µg total in both bands combined).

Notes:
1) Coomassie staining of $G_B$ is much weaker than for the pR58 fusion domain. Protein concentration was determined by $A_{280}$
2) Cleavage reaction was ~90% complete using this cleavage/elution protocol.

DETAILED DESCRIPTION OF THE INVENTION

The present invention relates to a prodomain comprising an optimized cognate sequence for binding to a highly specific processing subtilisin protease, wherein the pair has particular utility for protein purification.

The isolated subtilisin prodomain is unfolded but assumes a compact structure with a four-stranded anti parallel β-sheet and two three-turn α-helices in complex with subtilisin (Bryan P, et al., *Biochemistry* 1995, 34:10310-10318; Gallagher T D, et al., *Structure* 1995, 3:907-914) (FIG. 1). The C-terminal residues extend out from the central part of the prodomain and bind in a substrate-like manner along SBT's active site cleft. Residues Y77, A76, H75 and A74 of the prodomain become P1 to P4 substrate amino acids, respectively. These residues conform to subtilisin's natural sequence preferences. The folded prodomain has shape complementary and high affinity to native subtilisin mediated by both the substrate interactions of the C-terminal tail and a hydrophobic interface provided by the β-sheet (Gallagher T D, et al., *Structure* 1995, 3:907-914). The native tertiary structure of the prodomain is required for maximal binding to subtilisin. If mutations are introduced in regions of the prodomain, which do not directly contact subtilisin, their effects on binding to subtilisin are linked to whether or not they stabilize the native conformation. Therefore mutations which stabilize independent folding of the prodomain increase its binding affinity (Ruvinov S, et al., *Biochemistry* 1997, 36:10414-10421).

As used herein, the term "mutation" refers to an alteration in a gene sequence and/or an amino acid sequence produced by those gene sequences. Mutations include deletions, substitutions, and additions of amino acid residues to the wild-type protein sequence.

As used herein, the term "wild-type" refers to a protein, herein specifically a protease or prodomain, produced by unmutated organisms. Wild-type subtilisin-like proteases are produced by, for example, *Bacillus alcalophilus, Bacillus amyloliquefaciens, Bacillus amylosaccharicus, Bacillus licheniformis, Bacillus lentus,* and *Bacillus subtilis* microorganisms.

The term "variant" as used herein is defined as a protein in which the amino acid sequence, or other feature of a naturally occurring molecule has been modified and is intended to include mutants. Some of the variants falling within this invention possess amino acid substitutions deletions, and/or insertions provided that the final construct possesses the desired binding affinity between the protease prodomain and the corresponding protease Amino acid substitutions in the either the protease prodomain protein or the corresponding protease may be made on the basis of similarity in polarity, charge, solubility, hydrophobicity, hydrophilicity and/or the amphipathic nature of the residues involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine. Also included within the definition of variant are those proteins having additional amino acids at one or more sites of the C-terminal, N-terminal, as long as the variant retains the binding affinity.

The variants of the present invention may include subtilisin-like proteases. As used herein, the term "subtilisin-like protease" means a protease which has at least 25%, and preferably 80%, and more preferably 90% amino acid sequence identity with the sequences of subtilisin and maintaining at least the same functional activity of the wild-type protease.

The present invention is directed to the identification of a protease prodomain that is capable of binding a corresponding protease with high affinity. The protease prodomain of the present invention is fused to a second protein to form a protease prodomain fusion protein. The presence of a protease prodomain protein in a fusion protein allows for easy and selective purification of the second protein by incubation with the corresponding protease.

Examples of a second protein include, but are not limited to protein A, including *staphylococcal* Protein $A_B$ domain and Protein $A_B$ mutant A219; protein G including *Streptococcal* protein $G_B$ domain, *Streptococcal* protein $G_a$ domain and Protein $G_B$ mutant G311; *E. coli* hypothetical Yab; Bovine a-subunit of transducin; *M. thermautotrophicus* CDC6; streptavidin; avidin; Taq polymerase and other polymerases; alkaline phosphatase; RNase; DNase; various restriction enzymes; peroxidases; glucanases such as endo-1,4-beta glucanase, endo-1,3-beta-glucanase; chitinases, and others; beta and alfa glucosidases; beta and alpha glucoronidases; amylase; transferases such as glucosyl-transferases, phosphotransferases, chloramphenicol-acetyl-transferase; beta-lactamase and other antibiotic modifying and degrading enzymes; luciferase; esterases; lipases; proteases; bacteriocines; antibiotics; enzyme inhibitors; different growth factors; hormones; receptors; membranal proteins; nuclear proteins; transcriptional and translational factors and nucleic acid modifying enzymes.

The term "protease prodomain protein" refers to prodomain amino acid sequence or functional equivalent thereof wherein the protease prodomain protein possesses the capability of binding to a corresponding protease with high affinity. Preferably, the prodomain is substantially free of other proteins with which it is naturally associated, for instance, the balance of the protease protein. In addition, one or more predetermined amino acid residues in the prodomain may be substituted, inserted, or deleted, for example, to produce a prodomain protein having improved biological properties, or to vary binding and expression levels. Through the use of recombinant DNA technology, the prodomain proteins of the present invention having residue deletions, substitutions and/or insertions may be prepared by altering the underlying nucleic acid.

In one embodiment the protease prodomain protein may be fused to an antibody or an antigenic determinant as a second protein to form a protease prodomain fusion protein that is useful in diagnostic kits and in immunoassays. Thus, for example, bodily fluids can be tested for the presence of particular antibodies by making use of a protease prodomain and an antigenic epitope as a second protein fused to the protease prodomain protein. Conversely, an antigen or antigenic portions thereof can be detected using a protease prodomain and antibody fusion protein.

The term "fusion protein" as used herein refers to the joining together of at least two proteins, a prodomain protein, preferably being a protease prodomain and a second protein. Additionally, the fusion product of the present invention comprises an enzymatic cleavage site positioned between the protease prodomain and the second protein. The cleavage site if preferably adjacent to the N-terminus of the second protein thereby providing a means for recovering the second protein from the fusion product.

In another embodiment of the invention, the fusion protein is a recombinant fusion product. A "recombinant fusion product" is one that has been produced in a host cell that has been transformed or transfected with nucleic acid encoding the fusion product, or produces the fusion protein as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well as a cell within a host organism.

"Nucleic acid" refers to a nucleotide sequence comprising a series of nucleic acids in a 5' to 3' phosphodiester linkage that may be either an RNA or a DNA sequence. If the nucleic acid is DNA, the nucleotide sequence is either single or double stranded. The prodomain protease protein encoding nucleic acid is RNA or DNA that encodes a protein capable of binding the corresponding protease with high affinity, is complementary to nucleic acid sequence encoding such protein, or hybridizes to nucleic acid sequence encoding such protein and remains stably bound to it under stringent conditions.

In constructing the fusion protein expression vector, the nucleic acid encoding the prodomain will be linked or joined to the nucleic acid encoding the second protein such that the open reading frame of the protease prodomain protein and the second protein is intact, allowing translation of the fusion protein product to occur.

The nucleic acid encoding the prodomain protein of the present invention may be obtained from isolated and purified DNA from cell sources or by genomic cloning. Either cDNA or genomic libraries of clones may be prepared using techniques well known in the art and may be screened for particular protease or protease prodomain encoding nucleic acid with nucleotide probes that are substantially complementary to any portion of the gene. Alternatively, cDNA or genomic DNA may be used as templates for PCR cloning with suitable oligonucleotide primers. Full length clones, i.e., those containing the entire coding region of the desired protease prodomain protein may be selected for constructing expression vectors, or overlapping cDNAs can be ligated together to form a complete coding sequence. Alternatively, a preferred protease prodomain encoding DNA may be synthesized in whole or in part by chemical synthesis using techniques deemed to be standard in the art.

Methods for recombinant production of polypeptides are well known to those skilled in the art. Briefly, for example, host cells are transfected with a polynucleotide that encodes for a protease prodomain protein linked to a second protein of choice. Means of transforming or transfecting cells with exogenous polynucleotide such as DNA molecules are well known in the art and include techniques such as calcium-phosphate- or DEAE-dextran mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Following transfection, the cell is maintained under culture conditions for a period of time sufficient for expression of the fusion protein of the present invention. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C. pH is preferably from about a value of 6.0 to a value of about 8.0. Other biological conditions needed for transfection and expression of an encoded protein are well known in the art.

Transfected cells are maintained for a period of time sufficient for expression of the fusion protein and typically, maintenance time is from about 2 to about 14 days. When using recombinant techniques, the fusion protein can be produced intracellularly, in the periplasmic space, or directly secreted into the medium. If the polypeptide is produced intracellularly, as a first step, the particulate debris, either host cells or lysed cells (e.g. resulting from homogenization), is removed, for example, by centrifugation or ultrafiltration.

To direct a protease prodomain fusion protein of the present invention into the secretory pathway of the host cells, a secretory signal sequence (also known as a leader sequence or pre sequence) is usually required. In the present invention the prodomain sequence of the protease is part of the fusion protein and thus secretion of the fusion protein is easily effected by including a signal sequence such as that defined in SEQ ID NO. 2.

Thus, the recombinant fusion protein is recovered or collected either from the transfected cells or the medium in which those cells are cultured. The fusion protein is then subjected to one or more purification steps. In one embodiment of the invention, the recovery step involves exposing a composition comprising the fusion protein to a solid phase that has immobilized thereon a subtilisin or a variant thereof that binds with the prodomain protein with high affinity to form a protease/protease prodomain binding complex. The solid phase may be packed in a column and the immobilized corresponding protease captures the fusion protein and chemically and/or physically modifies the fusion protein to release the second protein.

By "solid phase" is meant a matrix comprising a protease to which a fusion product can adhere. The solid phase may be a purification column, a discontinuous phase of discrete particles, a membrane or filter. Examples of materials for forming the solid phase include polysaccharides (such as agarose and cellulose); and other mechanically stable matrices such as silica (e.g. controlled pore glass), poly(styrenedivinyl)benzene, polyacrylamide, ceramic particles and derivatives of any of the above. In preferred embodiments, the solid phase comprises controlled pore glass beads retained in a column that is coated with a protease for binding with high affinity for the prodomain protein of the fusion protein product.

The phrase "binding with high affinity" as used herein refers to the ability of the protease prodomain to bind to the cognate protease with a $K_d$ of nM to pM and ranging from about 10 nM to about 10 pM, preferably <100 pM.

This invention also relates to diagnostic detection of proteins of interest in test samples, especially in biological samples, such as tissue extracts or biological fluids, such as serum or urine through use of the fusion protein of the present invention. The biological samples are preferably of mammalian origin and most preferably of human origin. In one embodiment of the present invention, the fusion protein may comprise an antibody which is used to detect the presence of an antigen in biological samples using a variety of immunoassay formats well known in the art. Alternatively, the second protein of the fusion protein is comprised of an antigenic epitope useful in the detection of antibodies that recognize the antigenic determinant.

The "antibody" as used herein is meant to include polyclonal antibodies, monoclonal antibodies (MAbs), humanized or chimeric antibodies, single chain antibodies, anti-idiotypic (anti-Id) antibodies, and epitope-binding fragments of any of the above.

The term "detectable label" as used herein refers to any label which provides directly or indirectly a detectable signal and includes, for example, enzymes, radiolabelled molecules, fluoresors, particles, chemiluminesors, enzyme substrates or cofactors, enzyme inhibitors, magnetic particles. Examples of enzymes useful as detectable labels in the present invention include alkaline phosphatase and horse radish peroxidase. A variety of methods are available for linking the detectable labels to proteins of interest and include for example the use of a bifunctional agent, such as 4,4'-difluoro-3,3'-dinitro-phenylsulfone, for attaching an enzyme, for example, horse radish peroxidase, to a protein of interest. The attached detectable label is then allowed to react with a substrate yielding a reaction product which is detectable.

Also falling within the scope of the present invention is the therapeutic or diagnostic use of a protease prodomain fusion product wherein the second protein is a monoclonal antibody having affinity for an antigenic epitope. For example, a protease prodomain fusion product comprising (i) a protease prodomain capable of binding to a cognate protease with high affinity, and (ii) a monoclonal antibody capable of binding antigen can be used in a method to target a drug/protease complex or imaging agent/protease complex to a cancer cell producing the antigen. In this embodiment, a protease prodomain linked to a second protein (monoclonal antibody) is administered to a mammal. Either concurrently with or following the administration of the fusion product, a drug/protease or an imaging agent/protease complex is administered. Binding of the drug/protease or imaging agent/protease complex to the protease prodomain fusion product localized at the site of the antigen directs and targets the drug or imaging agent to the relevant site for the desired therapeutic or diagnostic activity.

The invention is further illustrated in the following examples, which are not intended to be in any way limiting to the scope of the invention as claimed.

Methods and Materials

Selection of Mutations, Cloning and Expression

The specific point mutations set forth in the present application identify the particular amino acids in the subtilisin BPN' amino acid sequence, as set forth in SEQUENCE ID NO: 3 (FIG. 2), that are mutated in accordance with the present invention. For example, the S149 mutant comprises a deletion of amino acids 75-83 and additionally comprises the following substitution mutations: Q2K, S3C, P5S, S9A, I31L, K43N, M50F, A73L, E156S, G166S. G169A, S188P, Q206C, N212G, K217L, N218S, T254A and Q271E. Additional mutated variants are set forth in Table 1 as shown in FIG. 3.

The subtilisin gene from *Bacillus amyloliquefaciens* (subtilisin BPN') had been cloned, sequenced, and expressed at high levels from its natural promoter sequences in *Bacillus subtilis* (Wells J A, et al., *Nucleic Acids Res.* 1983, 11:7911-7925; Vasantha N, et al., *J. Bacteriol.* 1984, 159:811-819). All mutant genes were recloned into a pUB110-based expression plasmid and used to transform *B. subtilis*. The *B. subtilis* strain used as the host contains a chromosomal deletion of its subtilisin gene and therefore produces no background wild type (wt) activity (Fahnestock et al., *Appl. Environ. Microbial.* 53:379-384 (1987)). Oligonucleotide mutagenesis was carried out as previously described. (Bryan P, et al., *Proc. Natl. Acad. Sci. USA* 1986, 83:3743-3745).

Wild type subtilisin and the variant enzymes were purified and verified for homogeneity essentially as described in Bryan et al., (Bryan P, et al., *Proc. Natl. Acad. Sci. USA* 1986, 83:3743-3745; Pantoliano M W, et al., *Biochemistry* 1987, 26:2077-2082; Pantoliano M W, et al., *Biochemistry* 1988, 27:8311-8317). In some cases the C221 mutant subtilisins were re-purified on a sulfhydryl specific mercury affinity column (Affi-gel 501, Biorad).

Cloning and Expression of the Prodomain of Subtilisin

The prodomain region of the subtilisin BPN' gene was subcloned using the polymerase chain reaction as described in Strausberg, et al. (Strausberg S, et al., *Biochemistry* 1993, 32:8112-8119). Mutagenesis of the cloned prodomain gene was performed according to the oligonucleotide-directed in vitro mutagenesis system, version 2 (Amersham International plc)

EXAMPLE 1

To demonstrate the feasibility of prodomain-directed processing, a gene was constructed to direct the synthesis of a fusion of the pR8 prodomain onto the N-terminus of the 56 amino acid B domain ($G_B$) of *Streptococcal* Protein G. Prodomain pR8 (SEQ ID NO: 4), having the mutations at amino acid residues 16-21 (QTMSTM (SEQ ID NO:8)) which were replaced with SGIK (SEQ ID NO: 9) creating a two amino acid deletion in pR8, wherein S replaces Q16, G replaces T17, M18I replaces S19 and T20 and "K" replaces M21; along with additional substitutions A23C, K27Q, V37L, Q40C, H72K and H75K is independently stable and binds to subtilisin with ~100-times higher affinity than the wild type prodomain. Further, pR8 thus becomes the cognate sequence specifying the subtilisin cleavage site.

The fusion protein (1 μM) was mixed with 1 μM of wild type subtilisin. The fusion protein was rapidly and specifically cleaved to release $G_B$ from pR8. From the results several relevant observations were made including that: 1) The processing is a single turn-over reaction with strong product inhibition by pR8 at the end of a cycle; 2) The rate of a single cycle of cleavage is limited by the substrate binding rate ($1e^6$ $M^{-1}s^{-1}$); and 3) Processing is highly specific because $G_B$ is quite resistant to subtilisin activity.

EXAMPLE 2

Mutations to Decrease Subtilisin Activity Against Non-Cognate Sequences

Using pR8 to direct cleavage in and of itself does not create an optimal processing system because of subtilisin's high activity against non-cognate sequences. The next step was to engineer subtilisin to be less active against non-cognate sequences. The starting point for engineering a processing subtilisin was a mutant denoted S149: (Q2K, S3C, P5S, K43N, A73L, deletion of 75-83, E156S, G166S, G169A, S188P, Q206C, N212G, K217L, N218S, T254A and Q271E). S149 previously was engineered for high stability and ability to fold independently of the prodomain. These characteristics, while not essential, are highly desirable in a processing enzyme.

First, the mutations G128S and Y104A were introduced in S149 (denoted S160) to enlarge the S4 pocket (Gron H, et al., *Adv Exp Med Biol* 1996, 379:105-112; Rheinnecker M, et al., *Biochemistry* 1994, 33:221-225). The catalytic properties of S149 and S160 were analyzed against two fluorogenic substrates, sDVRAF-AMC and sDFRAM-AMC, using transient state kinetic methods. The enlarged S4 pocket in S160 coupled a pre-existing preference for M over F at the P1 position resulted in a 100-fold preference of sDFRAM-AMC (Ks=0.8 μM) over sDVRAF-AMC (Ks=83 μM). In comparison S149 prefers sDFRAM-AMC (Ks=1 μM) by five fold over sDVRAF-AMC (Ks=5 μM). Thus, a modified subtilisin could be engineered to increase preference for cognate sequences.

EXAMPLE 3

A version of pR8 was constructed with its last four amino acids (AHAY (SEQ ID NO: 13)) replaced with FRAM (SEQ ID NO: 14), denoted pR58 (SEQ ID NO: 6). pR58 inhibits S160 with a Ki of ~30 pM. An N-terminal fusion of pR58 onto the $G_B$ domain was found to bind to S160 with a substrate affinity (Ks) in the pM range, at least $10^5$-times greater than even the highly preferred pentapeptide substrate sDFRAM-AMC. Essentially the prodomain structure acts as an amplifier of the P1 and P4 sequence signals. Hydrolysis is limited to a single turn-over by strong product inhibition. Product inhibition is difficult to avoid in using high substrate affinity to direct specific cleavage because of the structural similarity between substrate and product. We therefore do not attempt to obviate this property. As will be described later, the single turn-over reaction can be exploited in applying the system to protein purification.

A modified version of S160 with S166G was also constructed (denoted S193). The mutant prefers F and Y as P4 and P1 amino acids, respectively.

The preferential binding of S160 to pR58-fusions relative to non-cognate sequences does not results in highly specific cleavage. The reason for this can be discerned by considering the following mechanism for a single catalytic cycle:

$$E + S \xrightarrow{k_1} \underset{k_{-1}}{\overleftarrow{\quad ES \quad}} \xrightarrow{k_2} EX + P$$

The rate of the release of product $dP/dt=k_2k_1[S]/(k_1[S]+k_{-1}+k_2)$.

In the reaction of sDFRAM-AMC with S160, the substrate off rate ($k_{-1}$) is ~10 $s^{-1}$ compared to an acylation rate ($k_2$) of 100 $s^{-1}$. In the reaction of pR58-$G_B$, the acylation rate is similar but $k_{-1}$ is five orders of magnitude smaller ($1\times10^{-4}$ $s^{-1}$). The $k_2$ term in the denominator of the rate equation is ≧10-times larger than the $k_{-1}$ term in both cases, however, Thus, $k_{-1}$ has little influence on the observed rate of product formation. Substrate affinity would become increasingly important, however, if the acylation rate were slow enough that equilibrium between enzyme and substrate were approximated. Slowing $k_2$ was accomplished with mutations in the catalytic amino acids (D32 in S190), (S221 in S194) and the oxyanion hole amino acid (N155 in S188) (see Table 1 in FIG. 3).

Mutations in the Active Site Nucleophile S221A.

Mutation of the active site serine nucleophile in S160 creates a mutant (S194) which binds pR58 fusion proteins with ≦10 pM affinity. The rate of binding is rapid (~$1\times10^6$ $M^{-1}$ $s^{-1}$), but S194 cleaves the fusion protein very slowly (<100 $hr^{-1}$). However, the mutant is useful for affinity purification of uncleaved fusion proteins.

Mutations in the Oxyanion Hole: N155L, N155Q.

Removal of the hydrogen bond which stabilizes the oxyanion of the transition state decreases the rate of the acylation reaction ($k_2$) by ~1000-fold. Processing of the pR58-GB fusion protein by N155 (S188 and S191) mutants is a slow, single turn-over reaction. After the single round of cleavage pR58 remains tightly bound to the enzyme. As explained above, this reduction in $k_2$ creates a large degree of sequence discrimination base on differential substrate binding.

Mutations in the Asp-His Couple: Creation of an Anion Switch.

Of particular usefulness were the mutations of D32. The carboxylate of D32 hydrogen bonds to the catalytic H64 and allows it to act as first a general base and then a general acid during acylation. Mutation of the catalytic Asp in trypsin created a drastic decrease in activity around neutral pH but a strongly hydroxide dependant alternative mechanism evident above pH 10 (Craik C S, et al., *Science* 1987, 237:909-913; Sprang S, et al., *Science* 1987, 237:905-909). The potential of creating a two stage reaction consisting of a binding step followed by a chemically-triggered cleavage step led to focus on mutations at D32. Consequently D32 was mutated to A, S, V, G, and T in S160 and S193. The sequence specificity of D32 mutants is extremely high with kcat/Km≦10 $M^{-1}$ $s^{-1}$ vs. sFRAM-AMC. The high specificity was also manifested by their inability to process pR8-$G_B$ and also their inability to autoprocess in vivo unless the P4 residue of the pro-sequence was mutated from A to F.

The kinetics of fusion protein pR58-$G_B$ cleavage are shown in Table 2:

| mutation<br>Rate (hr$^{-1}$) | D32A (S189)<br>0.18 | D32V (S196)<br>0.3 | D32S (S190)<br>1.4 |
|---|---|---|---|

Reaction in 0.1M KPi, pH 7.2, 23° C.

EXAMPLE 4

Particularly advantageous are processing proteases whose activity is triggered on demand. Ions which have been useful as triggers are OH— (pH), Cl— and F—. The tables summarize cleavage rates of various D32 mutants as a function of specific anion.

Rates vs. pH. for S189 and S190

| pH | 5.7 | 7.2 | 8.8 | 10.0 |
|---|---|---|---|---|
| S189 hr$^{-1}$ | 0.135 | 0.18 | 0.97 | 4 |
| S190 hr$^{-1}$ | 0.18 | 1 | 5 | ≧25 |

Reaction in 0.1M KPi, 23° C.

Rates vs. [Cl]. For S189

| [Cl] | 0 M | 0.5 M |
|---|---|---|
| S189 hr$^{-1}$ | 0.97 | 5 |

Reaction in 0.1M KPi, pH 8.8, 23° C.

Rates vs. [F]. For S189

| [F] | 0 mM | 1 mM | 10 mM | 100 mM |
|---|---|---|---|---|
| S189 min$^{-1}$ | 0.003 | 0.018 | 0.14 | 0.8 |

Reaction in 0.1M KPi, pH 7.2, 23° C.

Figure 4:
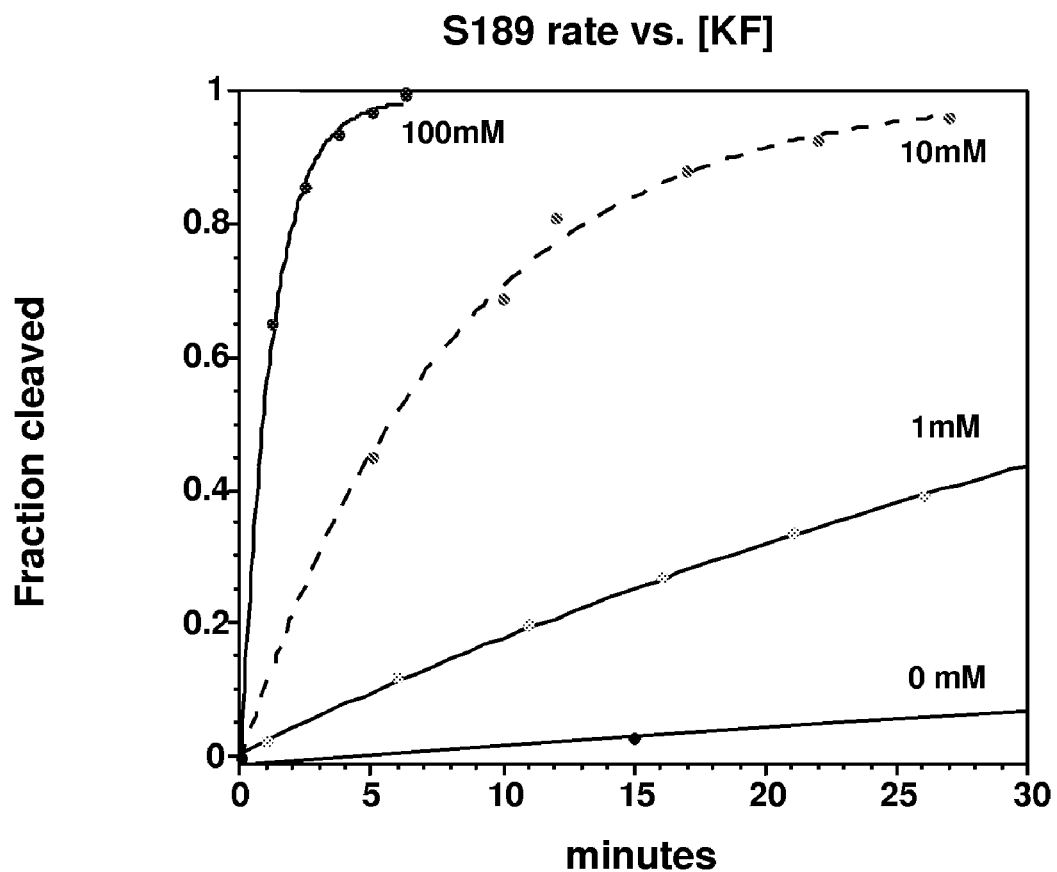
FIG. 4 shows the rate of protease processing proportional to the concentration of ions.

As shown in FIG. 4, the rate of activation is proportional to the concentration of the ions. Thus, S189 can be triggered to increase cleavage rates if desired and this can be very advantageous when required in a purification process. Once the fusion protein is bonded to the subtilisin variant to form a binding complex, the target protein can be cleaved from the prodomain protein by activation of the subtilisin variant with the introduction of an activating ion solution.

EXAMPLE 5

Truncation of the Prodomain

The prodomain of subtilisin can be replaced with a much shorter cognate sequence which has been selected for optimized binding with the processing protease. The amino acids comprising variations of only the C-terminal part of the prodomain (E E D K L (F/Y) Q S (M/L/Y) (SEQ ID NO: 7)) can be used as a cognate sequence. For example, it has been shown that the IgG binding domain of *Streptococcal* Protein G, which has no natural affinity to subtilisin, binds to S194 with a sub-micromolar dissociation constant once a nine amino acid C-terminal tail has been added.

EXAMPLE 6

Immobilization of Processing Subtilisins for Affinity Purification and Processing The binding and catalytic properties of processing subtilisin allows them to be used as both the affinity matrix and processing protease for purification of proteins tagged with the pR58 sequence. To demonstrate this point, S189 was immobilized on a chromatography resin.

Figure 5:
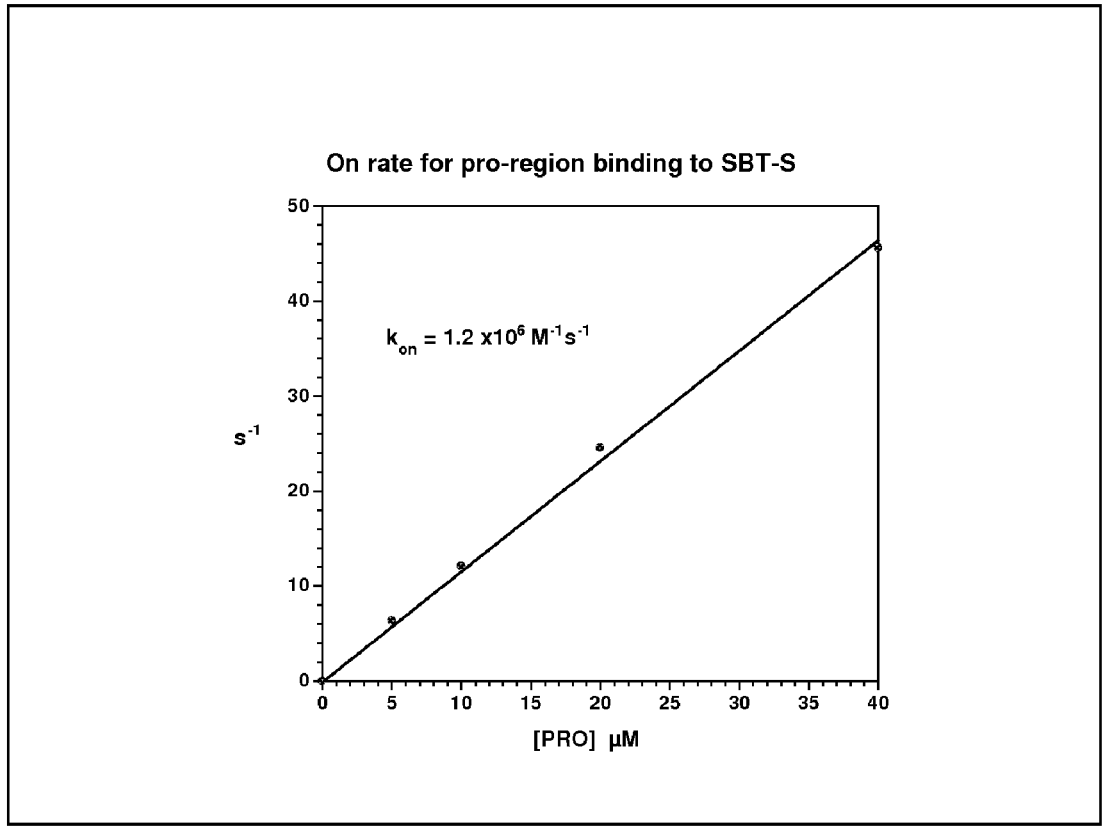
FIG. 5 shows that the rate of binding of processing subtilisin (S189) to the prodomain is rapid.
Figure 6:
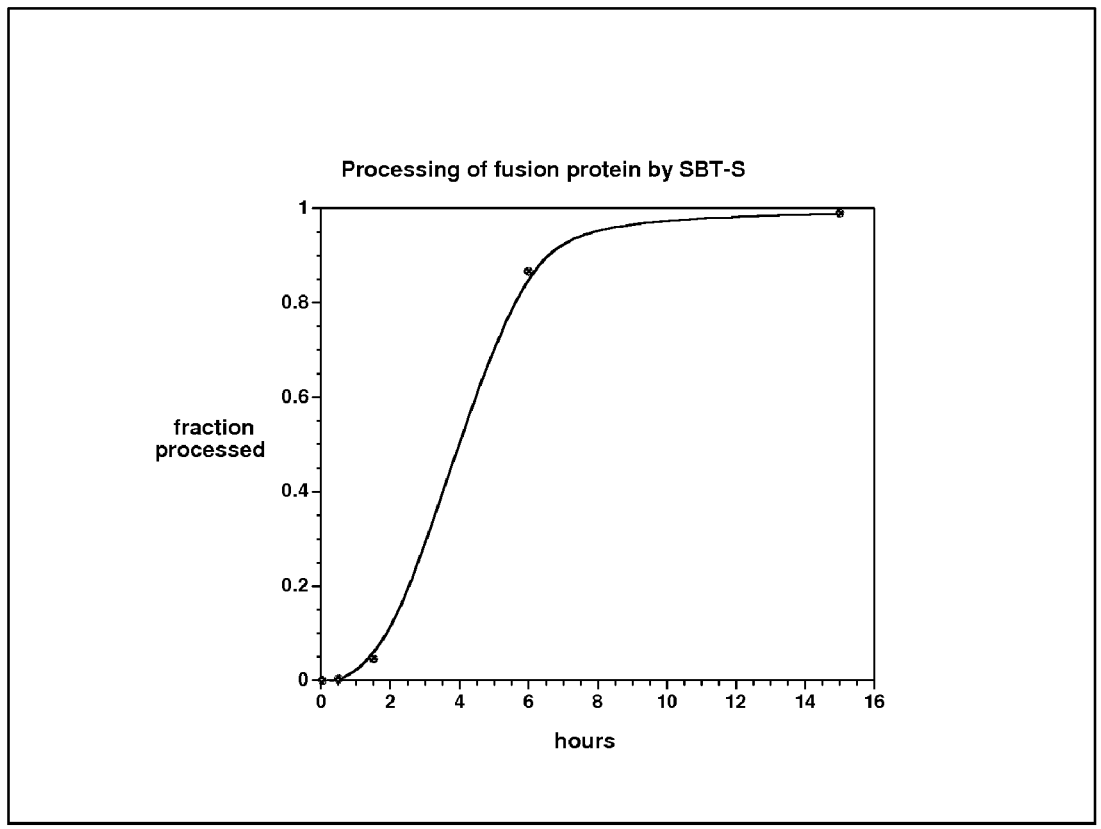
FIG. 6 shows that S189 cleaves with a half-time of about four hours. A lag phase is evident. This lag is useful for protein purification to allow contaminants to be washed away before significant cleavage has occurred.

An *E. coli* cell lysate containing pR58-$G_B$ was passed over the matrix containing immobilized S189. The fusion protein bound rapidly to the S189 matrix while the impurities were washed through the matrix as shown in FIG. 5. Cleavage of the bound fusion protein then was then effected either by addition of a triggering anion (e.g. 10 mM KF) or by extended incubation (e.g. 18 hours at pH 7.2) as shown in FIG. 6. After cleavage the pure, processed protein was washed off the matrix while the cognate prodomain remains tightly bound to subtilisin on the matrix. Multiple rounds of purification can be affected by stripping the pR58 from the S189 column at pH 2.1 and re-equilibrating the column at neutral pH. High stable and facile-folding mutants such as those listed in the Table 1 (FIG. 3) of Processing Subtilisin are required for column recycling.

Figure 7:
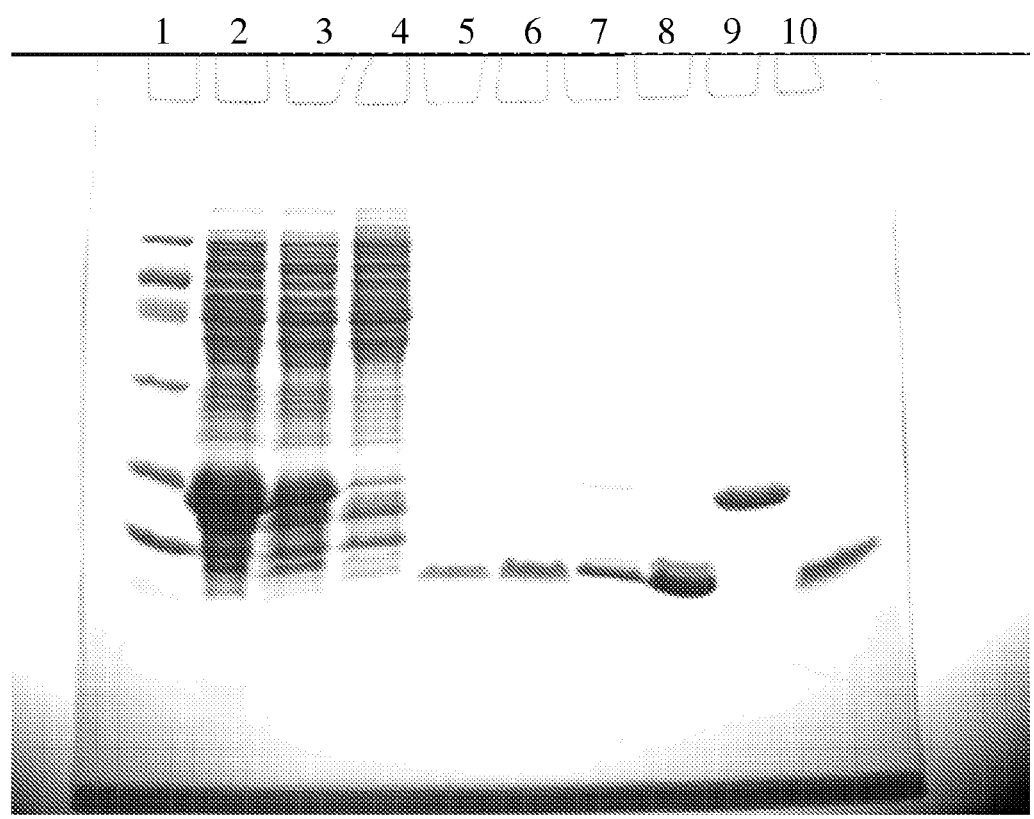
FIG. 7 shows the results of purification of a fusion protein comprising pr8FKAM-Protein G with immobilized substrate subtilisin S189 or 190 wherein the blot lanes are assigned as follows:
Lane 1: Molecular weight standards—2 μg band
Lane 2: cell lysate—10 μl of 10 ml from 250 ml culture of 671 pr8FKAM-Protein G
Lane 3: flow through from S189 AL loaded at 1 ml/min (10 μl fraction 2)
Lane 4: flow through from S190 AL loaded at 1 ml/min (10 μl fraction 2)
Lane 5: elution from S189 AL after 15 hours (10 μl fraction 2, 8 μg of protein G)
Lane 6: elution from S190 AL after 15 hours (10 μl fraction, 4.8 μg of protein G)
Lane 7: strip from S189 AL (10 μl fraction 7, 3 μg pR8FKAM)
Lane 8: strip from S190 AL (10 μl fraction 7, 9 μg pR8FKAM)
Lane 9: strip from S189 AL after ~10 minutes (10 μl fraction 6, 6.4 μg 671 FKAM)
Lane 10: $G_B$ standard

Eight different fusion proteins comprising pR58 and target proteins were purified and recovered in good yield by complexing the fusion protein with subtilisin S189 or S190, including:

*Streptococcal* protein $G_B$ domain 56 aa
*Streptococcal* protein $G_a$ domain 45 aa
Protein $G_B$ mutant G311 56 aa
*Staphylococcal* Protein $A_B$ domain 56 aa
Protein $A_B$ mutant A219 56 aa
*E. coli* hypothetical Yab 117 aa
Bovine a-subunit of transducin 350 aa
*M. thermautotrophicus* CDC6 379 aa As shown in FIG. 7, the fusion protein comprising pR58 (pR8FRAM) linked to *Streptococcal* protein $G_B$ domain was complexed and separated on both S189 and S190 immobilized beds. Lanes 3 and 4 show that multiple components of different molecular weights are washed through the system. After a sufficient incubation period, the fraction of output is limited to protein G, evidenced by the molecular weight fraction shown in lanes 5, 6, 7 and 8 relative to the molecular weight of protein G identified in lane 10.

Figure 8:
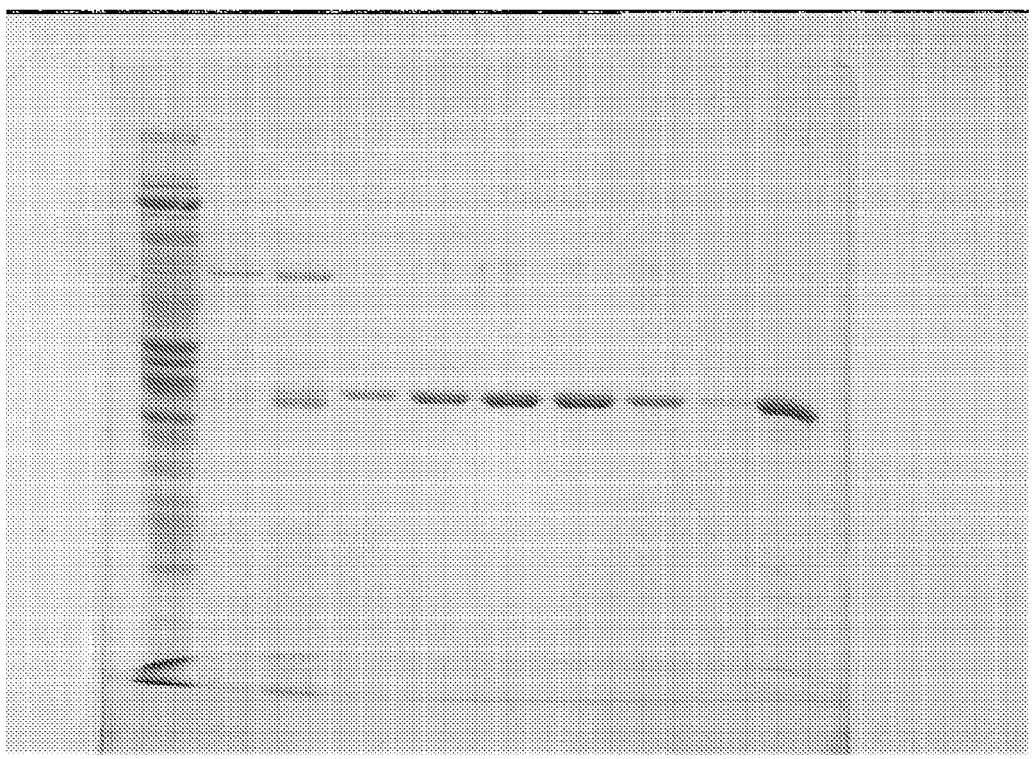
FIG. 8 shows purification results of α-subunit bovine transducin wherein the blot lanes are assigned as follows:
Lane 1: cell lysate—10 μl of 10 ml from 250 ml culture of 671 pr8FKAM-ChiT
Lanes 2-3: Column wash
Lanes 4-9: elution from S189 AL after 15 hours
Lane 10: pooled fractions

The results of the purification of β subunit bovine transducin (350aa) are shown in FIG. 8. As evidence by the elution shown in lanes 4-9, the target protein is eluted from the column after sufficient time for the cleaving the bond between the prodomain protein and the target protein by the activity of the subtilisin S189.

Figure 9:
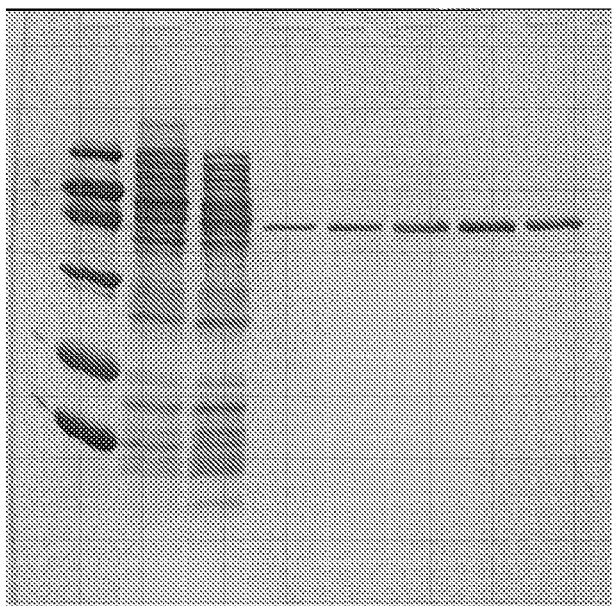
FIG. 9 shows purification results of M. Thermautotrophicus CDC6 wherein the blot lanes are assigned as follows:
Lane 1: Molecular weight standards—2 μg band
Lane 2: cell lysate—10 μl of 50 ml from 750 ml culture of pr8FKAM-CDC6
Lane 3: flow through from S189 AL__10 column loaded at 10 ml/min
Lanes 4-8: elution from S189 AL after 15 hours (10 μl fractions 2-6.

The results of purification of CDC6 (379 aa) are shown in FIG. 9. The fusion protein comprising pR58 (pR8FRAM) linked to *M. thermautotrophicus* CDC6 was complexed and separated on S189 immobilized beds. Lane 2 shows that multiple components of different molecular weights are washed through the system in the early period of separation. After a sufficient incubation period, the fraction of output is limited to CDC6, as evidenced by the molecular weight fraction shown in lanes 4-8.

Figure 10:
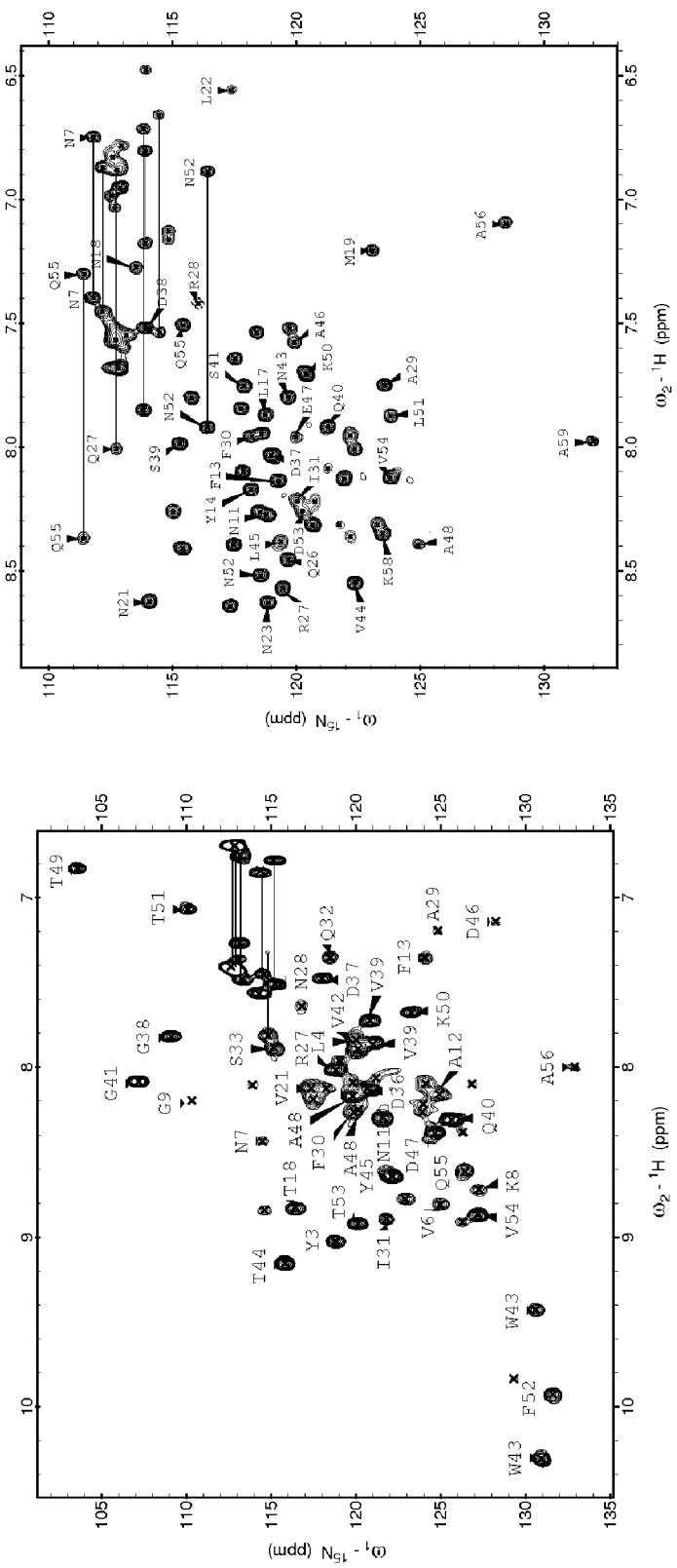
FIGS. 10 A and B shows the $^{15}$N HSQC spectra of (a) protein G311 and (b) protein A219 annotated with residue specific backbone assignments. The two proteins are 59% identical in sequence but represent different protein folds by NMR.

FIGS. 10 A and B show the $^{15}$N HSQC spectra of (a) protein G311 and (b) protein A219 that were purified on a S189AL_10 column and recovered therefrom. The two proteins are 59% identical in sequence but represent different protein folds.

EXAMPLE 7

Figure 11:
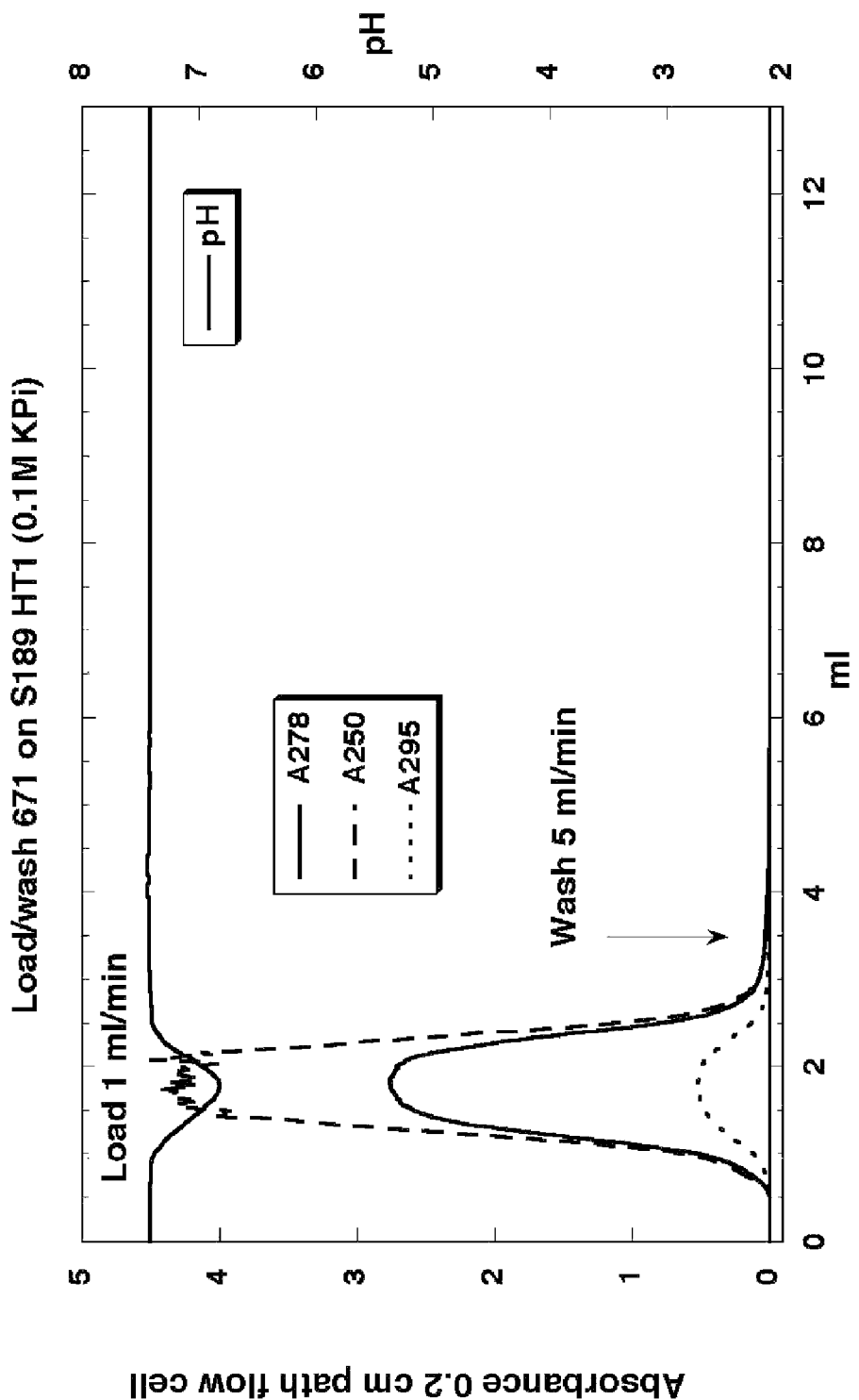
FIG. 11 shows the results of separation process of 56 amino acid $G_B$ from 671 fusion protein (pR58FKAM-$G_B$) on S189HiTrap NHS column when the fusion protein is bound and washed as in the normal procedure.
Figure 12:
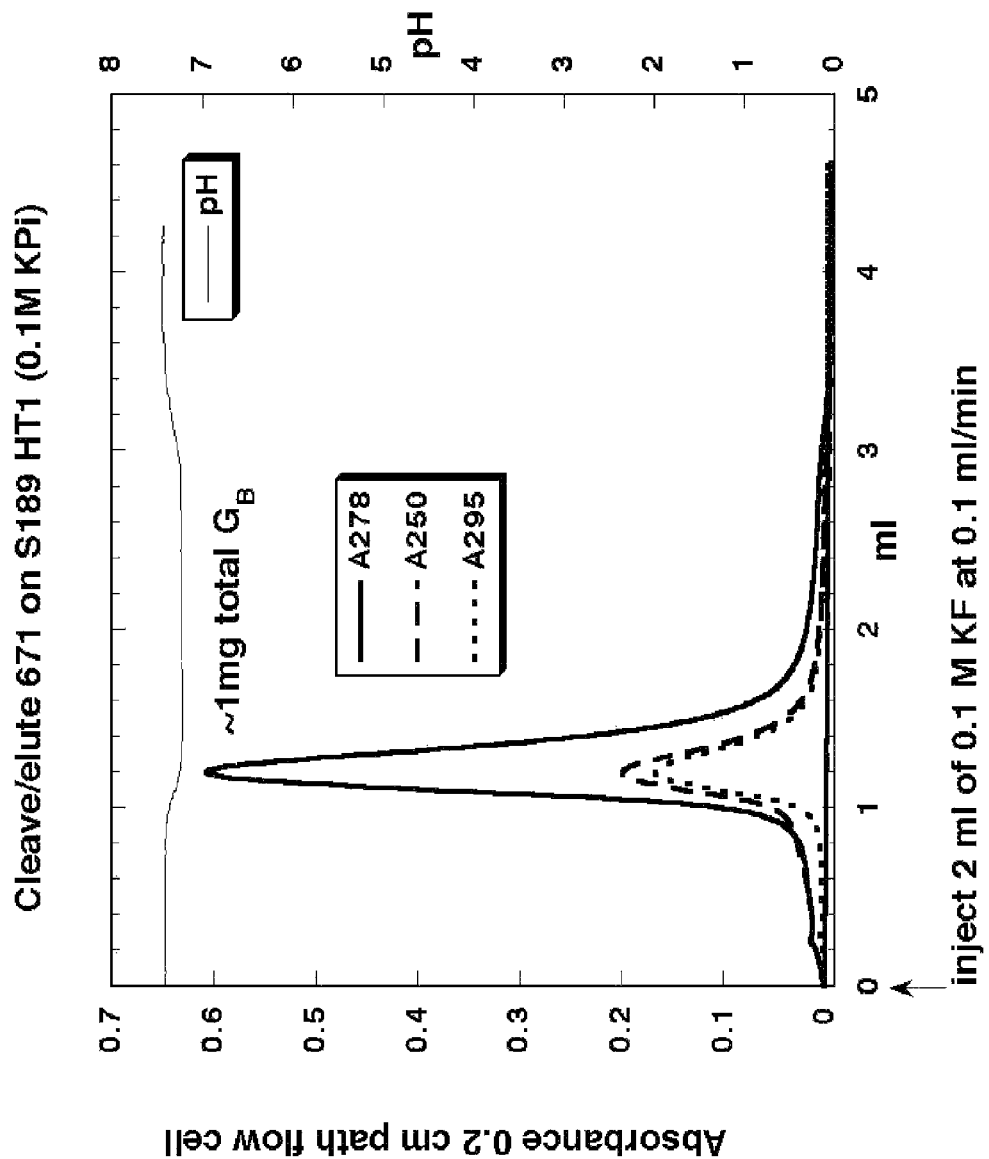
FIG. 12 shows the results when the release of the target protein is triggered by the addition of fluoride ions that decreases the time required for purification of the target protein.
Figure 13:
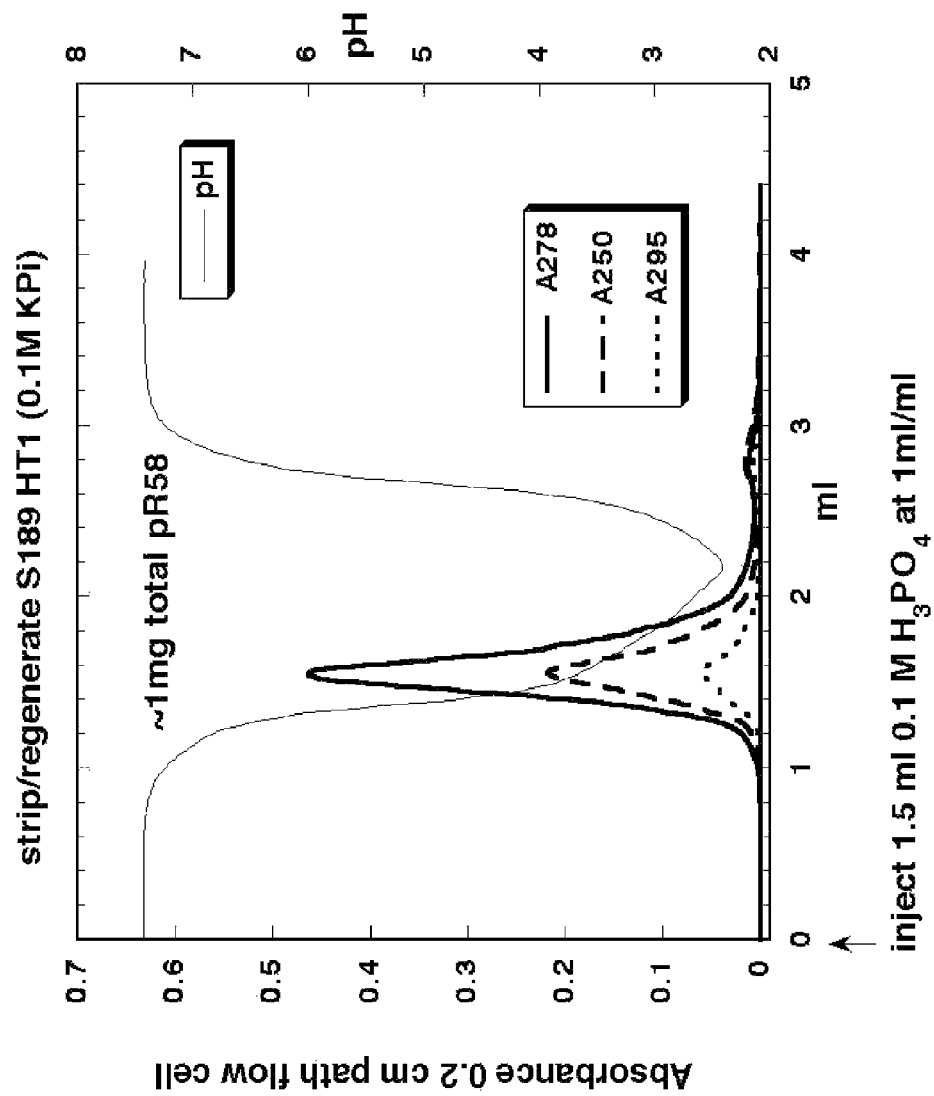
FIG. 13 shows the results when the prodomain (pR58) is stripped from the column in 0.1M $H_3PO_4$ as in the normal procedure.

Further purification experiments were conducted on the 56 amino acid *Streptococcal* protein $G_B$ domain linked to pR58 (pR8FRAM (SEQ ID NO: 6)) wherein the 671 fusion protein (pR58FKAM-$G_B$ (SEQ ID NO: 5)) was purified and separated on S189 HiTrap NHS column by continuous injection of 0.1M KF to demonstrate the effectiveness of the release of a target protein when mutant subtilisin was triggered by fluoride ions. FIG. 11 shows the results when the fusion protein is bound and washed as in the normal procedure. FIG. 12 show that the addition of 100 mM potassium fluoride injected at 0.1 ml/min causes the rapid cleavage as the fluoride ions come in contact with the bound fusion protein to release of the target protein so that it is concentrated as it is washed off the column. FIG. 13 shows that the stripping of the prodomain (pR58) from the column in 0.1M $H_3PO_4$ as in the normal procedure. These results show that the release of the target protein can be adjusted by the use of certain ions as triggers (OH— (pH), Cl— and F) to initiate the protease activity of the mutant subtilisins.

Figure 14:
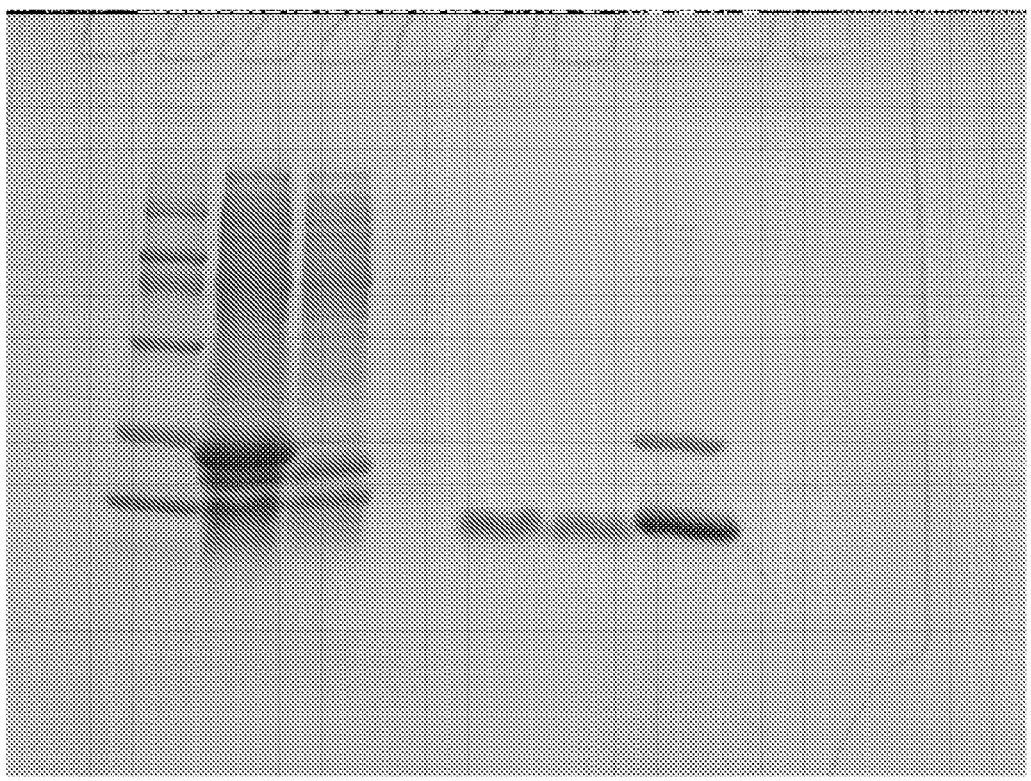
FIG. 14 shows purification results of *Streptococcal* protein $G_B$ when triggered by the addition of KF, wherein the blot lanes are assigned as follows.

FIG. 14 shows the separation of the fusion protein comprising pR58 (pR8FRAM) linked to *Streptococcal* protein $G_B$ domain on an S189 immobilized beds. Lane 1 is the molecular weight standards. Lanes 2 and 4 show that multiple components of different molecular weights as washed through the system. After the addition of 0.1M KF the fraction of output is limited to protein $G_B$, evidenced by the molecular weight fraction shown in lanes 5 and 6.

---

That which is claimed is:

1. An isolated subtilisin variant comprising subtilisin that is altered to bind to a fusion protein that comprises a protein of interest covalently bound by a peptide bond to the C-terminus of a subtilisin prodomain protein, wherein said subtilisin variant comprises a mutation at amino acid position 32 of SEQ ID NO:3, wherein the mutation at position 32 is selected from the group of amino acid substitutions consisting of D32A, D32S, D32V, D32G, and D32T, and the subtilisin variant cleaves the peptide bond between the protein of interest and the prodomain protein of the fusion protein upon incubation of the fusion protein with the subtilisin variant in the presence of a chemical trigger comprising anions.

2. The isolated subtilisin variant of claim 1, wherein the subtilisin variant further comprises a mutation at one or more of amino acid positions 2, 3, 5, 9, 31, 43, 50, 73, 75-83, 104, 126, 128, 155, 156, 166, 169, 188, 206, 212, 217, 218, 221, 254, and 271 of SEQ ID NO:3.

3. The isolated subtilisin variant of claim 1, wherein the subtilisin variant further comprises one or more of the following mutations: Q2K, S3C, P5S, S9A, I31 L, K43N, M50F, A73L, a deletion of the amino acids at positions 75-83, E156S, G166S, G169A, S188P, Q206C, N212G, K217L, N218S, T254A, Q271E, Y104A, G128S, L126I, N155L, N155Q, and S221A of SEQ ID NO:3.

4. The isolated subtilisin variant of claim 1, selected from the following subtilisin mutants of SEQ ID NO:3, subtilisin S189, subtilisin S190, subtilisin S196, subtilisin S197, subtilisin S198, subtilisin S199, and subtilisin S201.

5. A method for purifying a protein of interest comprising:
(i) contacting a fusion protein that comprises a protein of interest covalently bound by a peptide bond to the C-terminus of a subtilisin prodomain protein with a subtilisin variant that is altered to bind to such a fusion protein and comprises a mutation at amino acid position 32 of SEQ ID NO:3 wherein the mutation at amino acid position 32 of SEQ ID NO:3 is selected from the group of amino acid substitutions consisting of D32A, D32S, D32V, D32G, and D32T, whereby the subtilisin variant and the fusion protein form a binding complex;
(ii) incubating the binding complex with a chemical trigger comprising anions sufficient to cleave the protein of interest from the binding complex, wherein the subtilisin variant remains bound to the subtilisin prodomain protein; and
(iii) recovering the protein of interest.

6. The method of claim 5, wherein the isolated subtilisin variant further comprises a mutation at one or more of the amino acid positions 2, 3, 5, 9, 31, 43, 50, 73, 75-83, 104, 126, 128, 155, 156, 166, 169, 188, 206, 212, 217, 218, 221, 254, and 271 of SEQ ID NO:3.

7. The method of claim 5, wherein the isolated subtilisin variant further comprises one or more of the following mutations: Q2K, S3C, P5S, S9A, I31 L, K43N, M50F, A73L, a deletion of the amino acids at positions 75-83, E156S, G166S, G169A, S188P, Q206C, N212G, K217L, N218S, T254A, Q271E, Y104A, G128S, L126I, N155L, N155Q, and S221A of SEQ ID NO:3.

8. The method of claim 5, wherein the protein of interest is selected from among: staphylococcal Protein AB domain; Protein AB mutant A219; *Streptococcal* protein GB domain; *Streptococcal* protein Ga domain; Protein GB mutant G311; *E. coli* hypothetical Yab; Bovine α-subunit of transducin; *M. thermautotrophicus* CDC6; streptavidin; avidin; Taq polymerase; an alkaline phosphatase; a RNase; a DNase; a restriction enzyme; a peroxidase; an endo-1,4-β-glucanase; an endo-1,3-β-glucanase; a chitinase; a glucosidase; an α-glucosidase; a β-glucoronidase; an α-glucoronidase; an amylase; a glucosyl-transferase; a phospho-transferase; a chloramphenicol-acetyl-transferase; a β-lactamase; a luciferase; an esterase; a lipase; a protease; a bacteriocine; an antibiotic; an enzyme inhibitor; a growth factor; a hormone; a receptor; a membrane protein; a nuclear protein; a transcriptional factor; a translational factor; and a nucleic acid modifying enzyme.

* * * * *